(12) United States Patent
Al-Jazaeri et al.

(10) Patent No.: US 10,687,955 B2
(45) Date of Patent: Jun. 23, 2020

(54) DISTALLY EXPANDING FACET IMPLANT WITH INTEGRATED PLATE AND DELIVERY DEVICE

(71) Applicants: Ayman H. Al-Jazaeri, Riyadh (SA); Amro F. Al-Habib, Riyadh (SA)

(72) Inventors: Ayman H. Al-Jazaeri, Riyadh (SA); Amro F. Al-Habib, Riyadh (SA)

(*) Notice: Subject to any disclaimer, the term of this patent is extended or adjusted under 35 U.S.C. 154(b) by 141 days.

(21) Appl. No.: 15/887,457

(22) Filed: Feb. 2, 2018

(65) Prior Publication Data
US 2019/0240040 A1   Aug. 8, 2019

(51) Int. Cl.
| | |
|---|---|
| A61F 2/44 | (2006.01) |
| A61B 17/16 | (2006.01) |
| A61B 17/17 | (2006.01) |
| A61B 17/88 | (2006.01) |
| A61B 17/70 | (2006.01) |
| A61F 2/30 | (2006.01) |

(Continued)

(52) U.S. Cl.
CPC ........ *A61F 2/4405* (2013.01); *A61B 17/1671* (2013.01); *A61B 17/1735* (2013.01); *A61B 17/1757* (2013.01); *A61B 17/7062* (2013.01); *A61B 17/8894* (2013.01); *A61F 2/4611* (2013.01); *A61B 2017/0256* (2013.01); *A61F 2002/30265* (2013.01); *A61F 2002/30556* (2013.01); *A61F 2002/30579* (2013.01)

(58) Field of Classification Search
CPC ........ A62F 2/4405; A62F 2/44; A62F 2/4611; A61B 17/1671; A61B 17/1735; A61B 17/1757; A61B 17/7071; A61B 2002/443
See application file for complete search history.

(56) References Cited

U.S. PATENT DOCUMENTS

| | | | |
|---|---|---|---|
| 5,059,193 A | 10/1991 | Kuslich | |
| 5,665,122 A * | 9/1997 | Kambin | A61F 2/4455 411/55 |

(Continued)

*Primary Examiner* — Tessa M Matthews
(74) *Attorney, Agent, or Firm* — Neustel Law Offices

(57) ABSTRACT

A distally expanding facet implant with integrated plate and delivery device for distracting a cervical intervertebral facet joint to treat symptoms of degenerative processes of the cervical spine, including widening the intervertebral space and foramina while maintaining or restoring natural lordosis and preventing kyphosis. The distally expanding facet implant with integrated plate and delivery device generally includes opposed plates having distal and proximal ends, a diverting member having a stationary component and a moveable component comprising a diverting nut with a substantially fusiform cross-section between the plates, and a driving member comprising an elongated screw rotationally coupled with the moveable component. Rotation of the screw causes an engagement surface of the diverting nut to slide against a complementary engagement surface of the stationary component. The dimension of the nut present between the distal ends of the plates increases as the surfaces slide against each other causing the distal ends to divert without diverting the proximal ends. Deployed within a facet joint, the implant produces distraction of the facet joint and widening of the intervertebral spacing and foramina while maintaining natural lordosis and preventing kyphosis.

40 Claims, 15 Drawing Sheets

(51) Int. Cl.
*A61F 2/46* (2006.01)
*A61B 17/02* (2006.01)

(56) References Cited

U.S. PATENT DOCUMENTS

| | | | |
|---|---|---|---|
| 6,193,757 B1 * | 2/2001 | Foley | A61F 2/4455 623/17.16 |
| 6,491,724 B1 * | 12/2002 | Ferree | A61L 27/38 623/17.11 |
| 7,753,958 B2 | 7/2010 | Gordon | |
| 7,776,090 B2 | 8/2010 | Winslow | |
| 8,029,540 B2 | 10/2011 | Winslow | |
| 8,267,966 B2 | 9/2012 | McCormack | |
| 8,361,152 B2 | 1/2013 | McCormack | |
| 8,512,347 B2 | 8/2013 | McCormack | |
| 8,753,345 B2 | 6/2014 | McCormack | |
| 8,834,472 B2 | 9/2014 | McCormack | |
| 8,845,728 B1 * | 9/2014 | Abdou | A61F 2/4455 623/17.11 |
| 9,005,288 B2 | 4/2015 | McCormack | |
| 9,011,492 B2 | 4/2015 | McCormack | |
| 9,044,277 B2 | 6/2015 | O'Neil | |
| 9,131,965 B2 | 9/2015 | Prewett | |
| D745,156 S | 12/2015 | McCormack | |
| 9,308,091 B2 | 4/2016 | Lang | |
| 9,333,086 B2 | 5/2016 | McCormack | |
| 9,381,049 B2 | 7/2016 | McCormack | |
| 9,622,873 B2 | 4/2017 | McCormack | |
| 9,629,665 B2 | 4/2017 | McCormack | |
| 9,649,138 B2 | 5/2017 | Altarac | |
| 10,022,239 B1 * | 7/2018 | Lentner | A61F 2/4425 |
| 10,327,909 B2 * | 6/2019 | Baynham | A61F 2/4425 |
| 2004/0215198 A1 * | 10/2004 | Marnay | A61B 17/1604 606/86 R |
| 2006/0167456 A1 * | 7/2006 | Johnston | A61B 17/1728 606/86 B |
| 2011/0035011 A1 * | 2/2011 | Cain | A61F 2/442 623/17.16 |
| 2012/0226357 A1 * | 9/2012 | Varela | A61F 2/447 623/17.16 |
| 2014/0194886 A1 * | 7/2014 | Poulos | A61B 17/864 606/94 |
| 2014/0257486 A1 * | 9/2014 | Alheidt | A61F 2/447 623/17.15 |
| 2014/0277460 A1 * | 9/2014 | Schifano | A61F 2/4611 623/17.11 |
| 2015/0342648 A1 | 12/2015 | McCormack | |
| 2015/0351923 A1 * | 12/2015 | Emstad | A61F 2/30771 623/17.16 |
| 2016/0022438 A1 * | 1/2016 | Lamborne | A61F 2/4455 623/17.16 |
| 2016/0374740 A1 * | 12/2016 | Donald | A61B 17/864 606/304 |
| 2017/0056197 A1 * | 3/2017 | Weiman | A61F 2/447 |
| 2019/0133784 A1 * | 5/2019 | Gunn | A61F 2/4455 |

\* cited by examiner

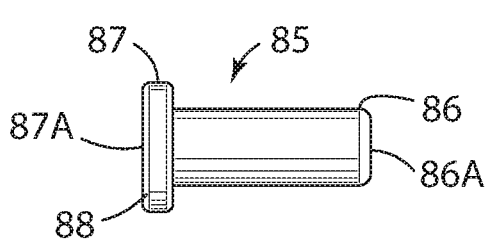
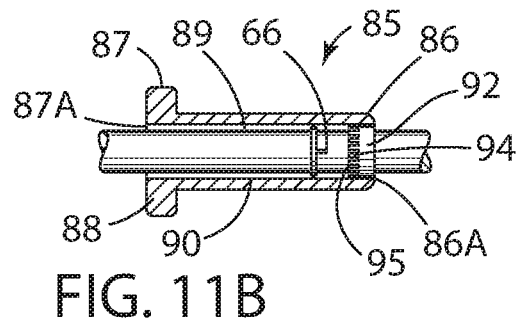
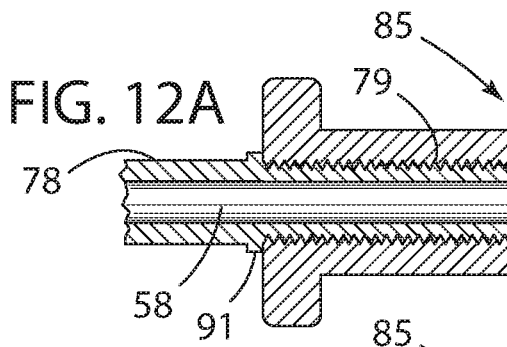
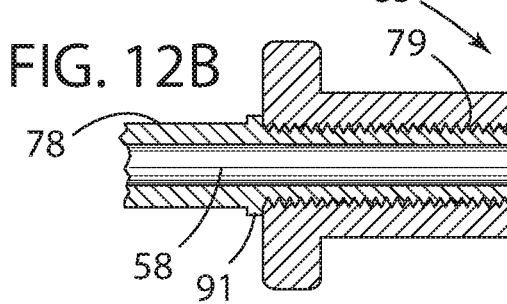
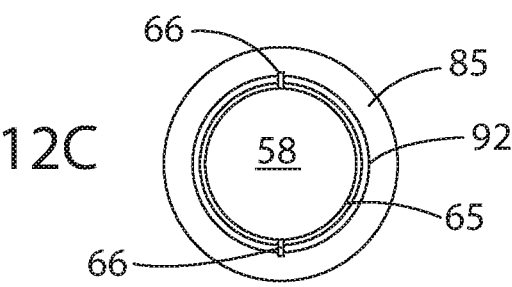
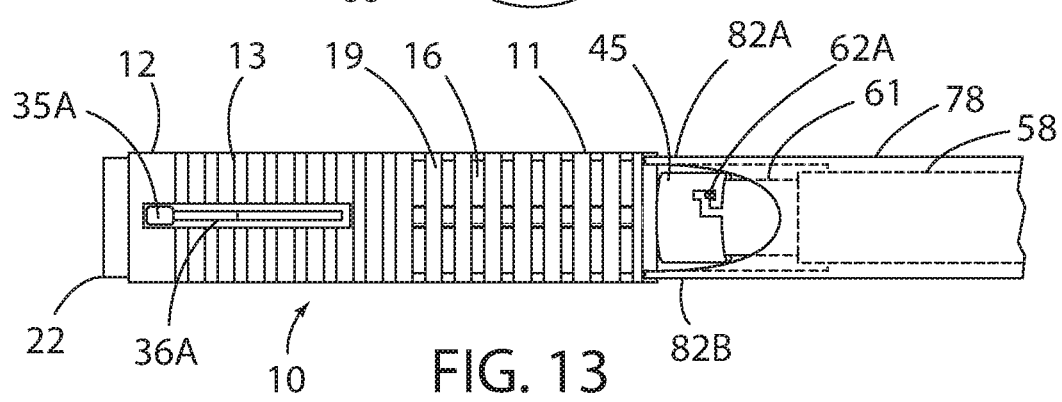

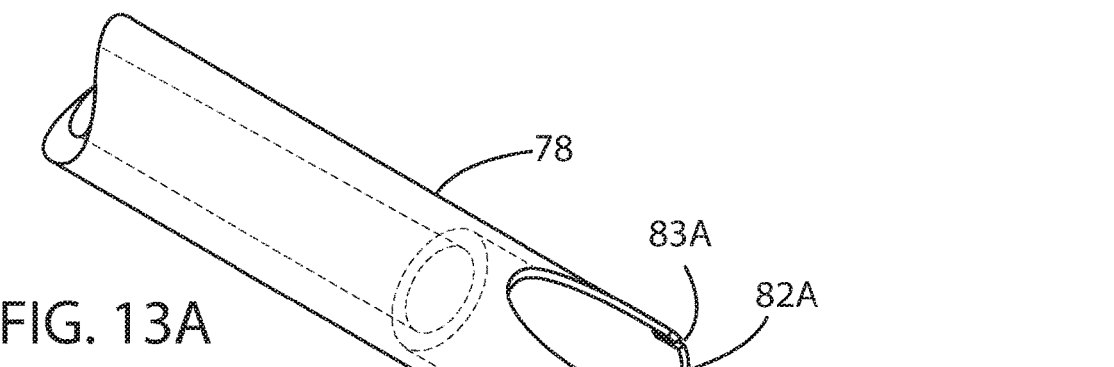
FIG. 13A
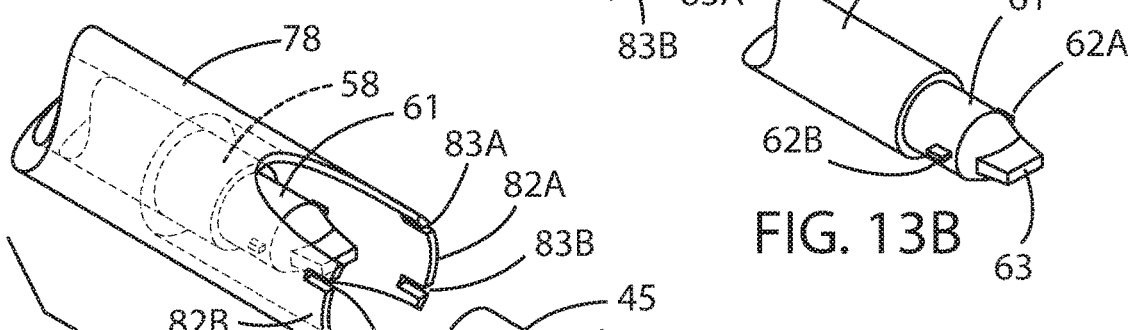
FIG. 13B
FIG. 13C
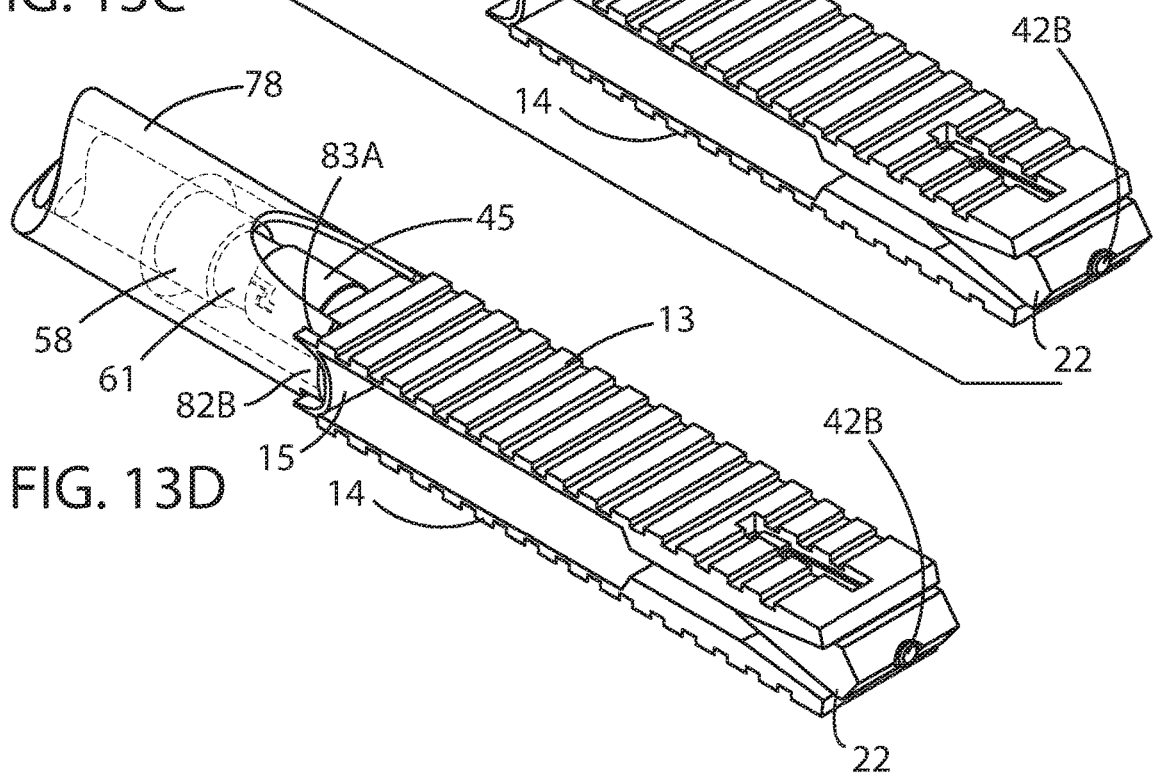
FIG. 13D

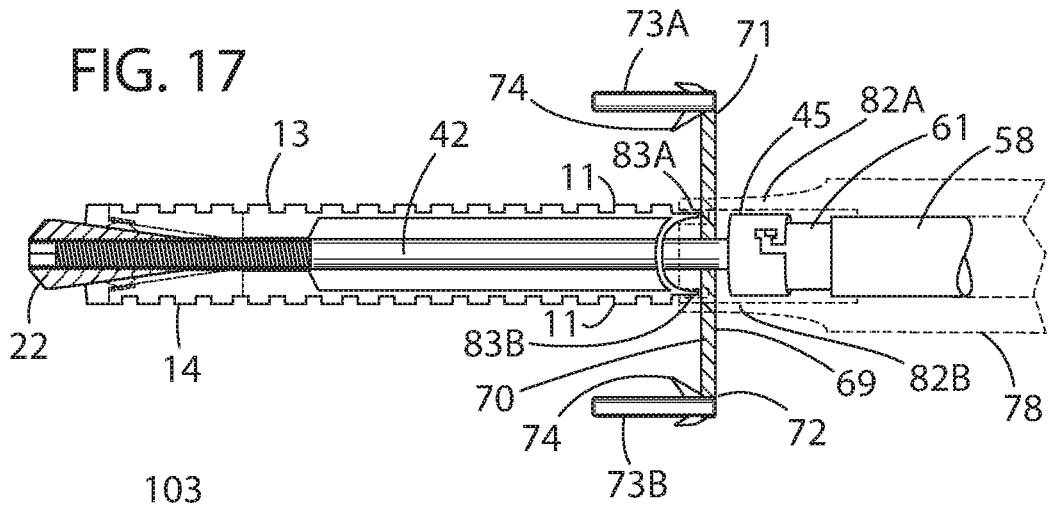
FIG. 17
FIG. 18
FIG. 19C
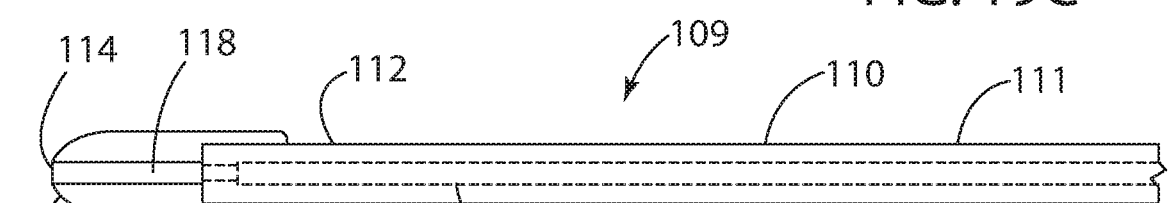
FIG. 19A
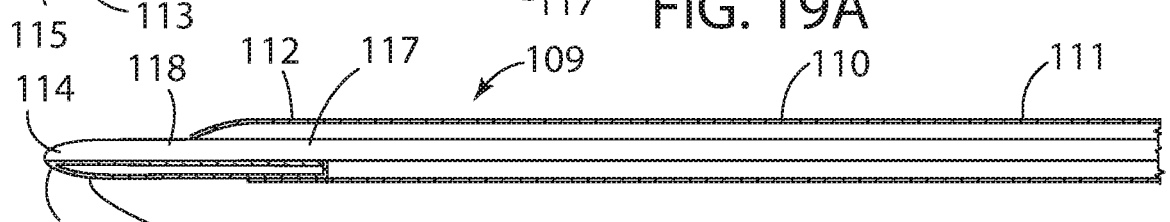
FIG. 19B

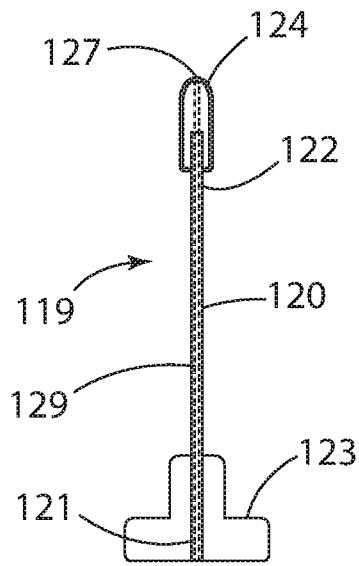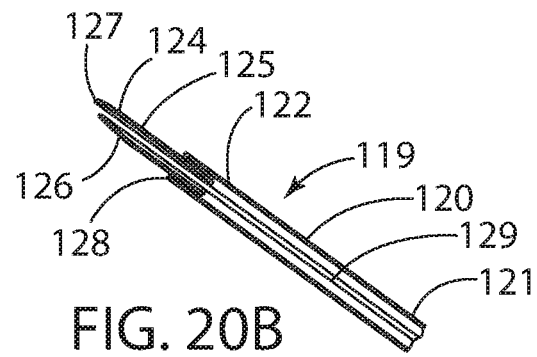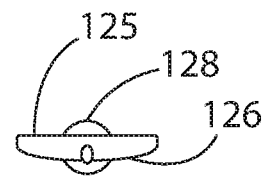
FIG. 20A  FIG. 20B  FIG. 20c
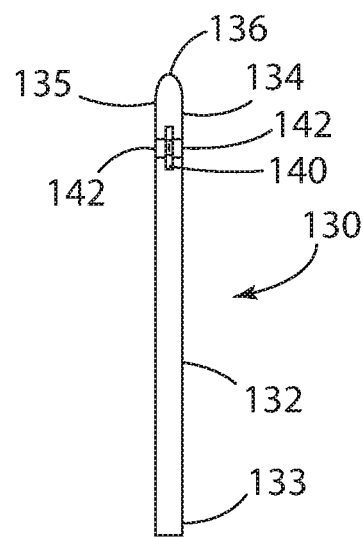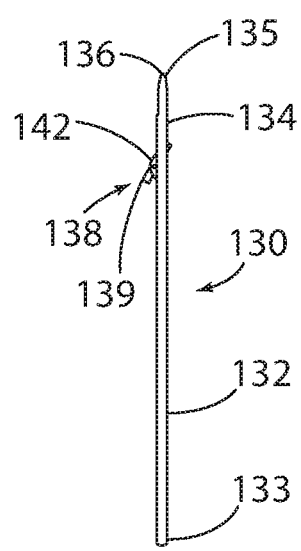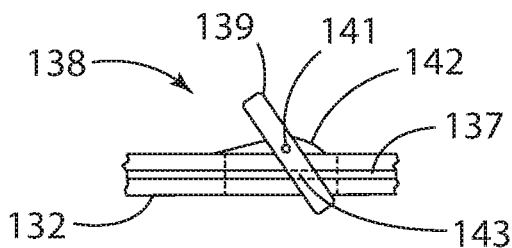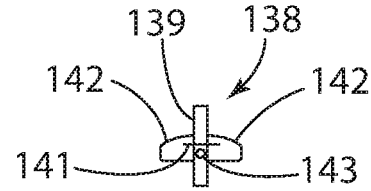
FIG. 21A  FIG. 21B  FIG. 21C  FIG. 21D

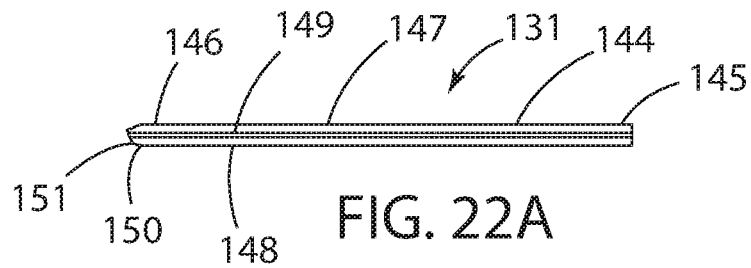
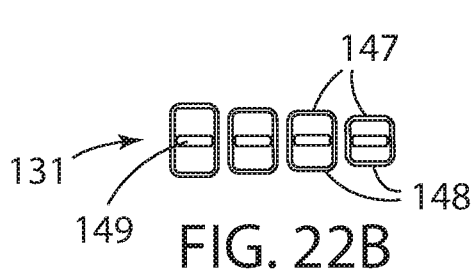
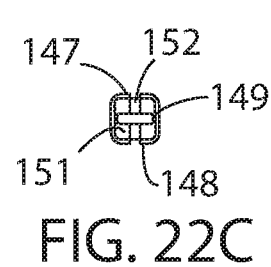
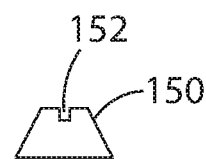
FIG. 22A
FIG. 22B   FIG. 22C   FIG. 22D
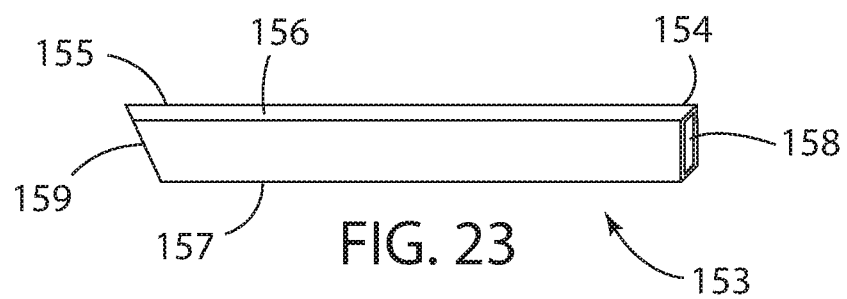
FIG. 23
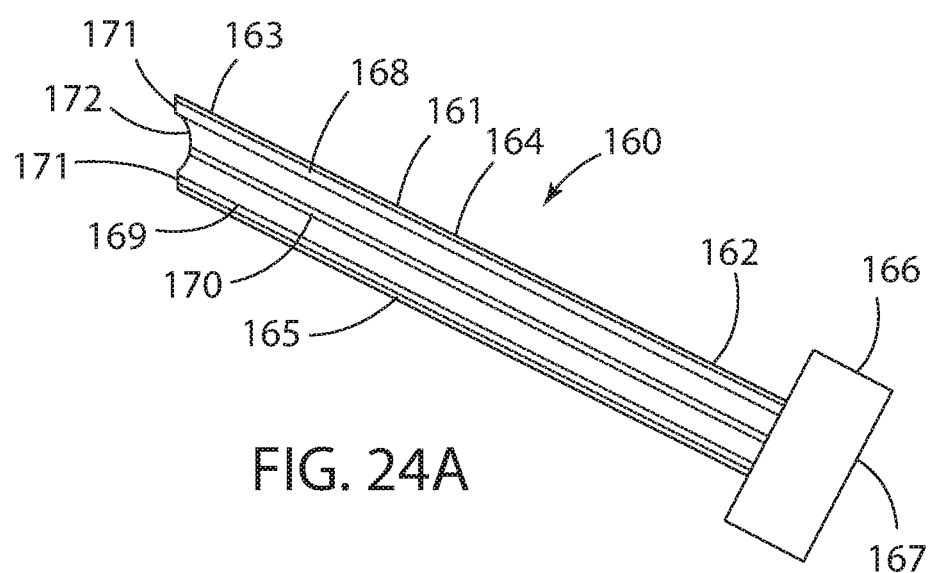
FIG. 24A

DISTALLY EXPANDING FACET IMPLANT WITH INTEGRATED PLATE AND DELIVERY DEVICE

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND

Field

Example embodiments in general relate to a distally expanding facet implant with integrated plate and delivery device for distracting adjacent bony bodies, including adjacent vertebrae, and more particularly adjacent cervical vertebrae separated by a facet joint, while maintaining or improving cervical spine lordosis.

Related Art

Any discussion of the related art throughout the specification should in no way be considered as an admission that such related art is widely known or forms part of common general knowledge in the field.

Spine degeneration is a major burden to society. The current growth of the aging population is linked to a rise in cases of age-related spine joint degenerative change or arthropathy, which is a leading cause of chronic neck and back pain. The socioeconomic costs of degenerative spine disease are large. Such costs include both direct costs, such as payments for treatment of pain and neurologic disorders, and indirect costs from loss of work and frequent sick leaves.

The spinal column is composed of 33 vertebrae, separated by intervertebral discs and held together with ligaments and muscles. The spinal column provides an axial support for the human body in addition to its function as a protector to the spinal cord and its emerging nerve roots. Movement within each spine segment (two adjacent vertebrae) is facilitated by the anteriorly located intervertebral discs and two posterior facet joints. The series of these joints between adjacent vertebrae of the spinal column permit the complex flexible movements of the spinal column.

The aging process often leads to degenerative changes that impact the structure of the spine joints. The process involves dehydration of the intervertebral discs resulting in reduction of disc height. Subsequently, friction between the joint surfaces occurs and a process of degeneration and local inflammation begins. The joints then become stiffer and the ligaments become thickened and less elastic. The overall process is collectively named spondylosis. Spondylosis leads to reduction in the size of the neural foramens (the space where the nerves emerge from the spinal cord), disc herniation, and spinal stenosis resulting in axial neck and/or back pain and neurological compromise. As the degenerative changes advance and the intervertebral foramen narrowing progresses, compression of the nerve roots can occur leading to nerve damage. Such damage often manifests itself as numbness and weakness due to motor and sensory function loss in addition to persistent pain in what is called radiculopathy. Radiculopathy resulting from damage to the cervical nerve roots is referred to more particularly as cervical radiculopathy.

The main goal in treating radiculopathy is to decompress the affected nerve. This goal can be accomplished by direct nerve decompression and removal of the compressing element, or by distracting away from each other two adjacent vertebrae compressing the nerve. The two approaches are frequently combined. Typically, either an anterior procedure is performed that involves the removal of the collapsed intervertebral disc and replacement with a bone or synthetic cage, or a posterior procedure that involves laminectomy with or without facetectomy (facet removal). In either case, the procedure is often coupled with the addition of instrumentation between the involved vertebrae to stabilize them and facilitate their fusion together.

With respect to the cervical spine in particular, evidence has highlighted the importance of maintaining the natural cervical spine lordosis during surgical treatment of cervical radiculopathy as maintaining the natural lordosis is often associated with better neurological functional outcomes. Thus, surgical treatment of the cervical spine to counteract the effects of the degenerative process must incorporate cervical alignment to achieve the most beneficial outcome. While current anterior surgical procedures have been demonstrated to be effective in maintaining or restoring natural lordosis to the cervical spine, current posterior procedures have been associated with a worsening of lordosis, i.e. increased kyphosis.

At the same time, the current trend is to employ minimally invasive surgical approaches to treat various spinal diseases because such approaches have been demonstrated to lead to less post-operative pain, less surgical blood loss, and earlier recovery from surgery. For treatment of cervical radiculopathy, the commonly performed minimally invasive technique utilizes the posterior approach and specially designed devices to distract the facet joint by inserting an implant inside the facet joint and, consequently, relieving the nerve root compression. However, to date such devices have not achieved substantial success in providing optimal distraction of the facet joint while at the same time maintaining or restoring the natural lordosis of the cervical spine and avoiding inducing kyphosis.

SUMMARY

An example embodiment is directed to a distally expanding facet implant with integrated plate and delivery device for distracting a cervical intervertebral facet joint to treat symptoms of degenerative processes of the cervical spine, including widening the intervertebral space between adjacent vertebrae and the foramina while maintaining or restoring natural lordosis and preventing kyphosis.

The distally expanding facet implant with integrated plate and delivery device generally comprises a pair of plates each having a first and second end, a diverting member adapted for moveable engagement with the plates, and a driving member coupled with the diverting member and operable to cause the diverting member to move in engagement with the plates to cause the plates to divert away from each other at and near their respective first ends without causing any substantial diversion of the second ends. As a result, when the implant is deployed in a cervical intervertebral facet joint with the first ends of the plates located anteriorly and the second ends located posteriorly, operation of the driving member causes distraction of the facet joint and widening of the intervertebral space and foramina while maintaining or restoring the natural lordosis of the cervical spine and without inducing kyphosis.

In one aspect, the diverting member is positioned between the plates and comprises a stationary component connected to the plates and a moveable component adapted for moveable engagement with the stationary component. The driving member is coupled with the moveable component. More particularly, the driving member may comprise a screw adapted for rotation, the moveable component may comprise a diverting nut having a substantially fusiform cross-sectional shape, and the screw may be rotatably coupled with the diverting nut. The stationary and moveable components may have complementary engagement surfaces adapted for moveable engagement, which may include sliding engagement, and the surfaces may comprise complementary angled sloped surfaces.

Operation of the driving member causes the engagement surface of the moveable component to moveably engage the complementary engagement surface of the stationary component causing the plates to divert away from each other at and near the first ends without causing the second ends to divert substantially. In a particular embodiment, rotation of the screw causes the engagement surface of the diverting nut to slide against the engagement surface of the stationary component. As the engagement surface of the diverting nut slides against the engagement surface of the stationary component, the dimension of the diverting nut present between the first ends of the plates increases causing the first ends to divert without substantially diverting the second ends.

In another aspect, wherein the driving member comprises an elongated screw adapted for rotation, the screw comprises a head adapted for engagement by a screwdriver to impart rotational motion to the screw. The head comprises a function selection slot with positions corresponding to rotation or pulling of the screw. The screwdriver comprises a pin adapted to engage the function selection slot and to be selectively moveable within the slot between the positions corresponding to rotation and pulling of the screw. The screwdriver also comprises a drive head adapted to engage the head of the screw to impart rotational movement to the screw when the pin is in the position corresponding to rotation of the screw.

In another aspect, the implant comprises an inter-facet plate. The inter-facet plate is engaged with the driving member and is adapted to be fastened to the external posterior facet surfaces of vertebrae adjacent the cervical intervertebral facet joint in an orientation substantially perpendicular to the plates of the implant when the implant is deployed in the joint. The inter-facet plate responds to the driving member being operated to divert the plates of the implant, which may comprise rotating a drive screw, to substantially simultaneously lock the external posterior facets of the adjacent vertebrae together to prevent posterior distraction of the facet joint. Thus, in response to operation of the driving member the inter-facet plate facilitates distraction of the facet joint and widening of the intervertebral space and foramina without inducing kyphosis of the cervical spine.

In still another aspect, a device is adapted to hold the implant for delivery to and insertion in the cervical intervertebral facet joint. The device comprises an elongated sheath having a first end, a second end, and an interior passage, and a handle having an interior passage. The first end of the elongated sheath comprises a holding arm adapted to engage and hold the implant. The second end of the elongated sheath is coupled with the handle with the interior passages of the handle and the elongated sheath in communication. The screwdriver is moveably coupled with the handle and extends through the interior passages of the handle and elongated sheath such that the screwdriver can be manipulated to selectively extend the pin and drive head of the screwdriver beyond the holding arm for engaging the head of the screw of the implant while the implant is held by the holding arm.

In yet another aspect, an elongated guide plate provides a means to deliver various tools to the facet joint to prepare the joint to receive the implant. The guide plate includes a stop mechanism to ensure proper positioning and prevent over insertion in the facet joint. The joint preparation tools include a dilator, a special chisel and rasp, and a drill guide, all adapted to cooperate with the guide plate.

There has thus been outlined, rather broadly, some of the embodiments of the distally expanding facet implant with integrated plate and delivery device in order that the detailed description thereof may be better understood, and in order that the present contribution to the art may be better appreciated. There are additional embodiments of the distally expanding facet implant with integrated plate and delivery device that will be described hereinafter and that will form the subject matter of the claims appended hereto. In this respect, before explaining at least one embodiment of the distally expanding facet implant with integrated plate and delivery device in detail, it is to be understood that the distally expanding facet implant with integrated plate and delivery device is not limited in its application to the details of construction or to the arrangements of the components set forth in the following description or illustrated in the drawings. The distally expanding facet implant with integrated plate and delivery device is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

FIG. 11A is a top plan view of the assembly handle of the implant-screwdriver holding sheath assembly of FIG. 10 in accordance with an example embodiment of a distally expanding facet implant with integrated plate and delivery device.

FIG. 11B is a partial longitudinal cross-sectional view showing the interior of the assembly handle of FIG. 11A in accordance with an example embodiment of a distally expanding facet implant with integrated plate and delivery device.

FIG. 12A is a partial side view showing an implant-screwdriver holding sheath assembly with the implant holding sheath mounted in the assembly handle with the holding sheath and assembly handle illustrated in cross-section to show the screwdriver in a locked position in accordance with an example embodiment of a distally expanding facet implant with integrated plate and delivery device.

FIG. 12B is a partial side view of the implant-screwdriver holding sheath assembly as shown in FIG. 12A with the implant holding sheath and assembly handle illustrated in cross-section to show the screwdriver in an unlocked position in accordance with an example embodiment of a distally expanding facet implant with integrated plate and delivery device.

FIG. 12C is a transverse cross-sectional view of the implant-screwdriver holding sheath assembly as shown in FIG. 12A in accordance with an example embodiment of a distally expanding facet implant with integrated plate and delivery device.

FIG. 13 is a partial top plan view showing a facet implant held by an implant-screwdriver holding sheath assembly with the implant holding sheath illustrated in longitudinal cross-section to reveal the interconnections of the facet implant, facet implant screw, screwdriver, and implant holding sheath in accordance with an example embodiment of a distally expanding facet implant with integrated plate and delivery device.

FIG. 13A is a partial perspective view of the distal end of an implant holding sheath and implant holder and with the holding sheath illustrated partially transparent to show a shaft for passage of a screwdriver in accordance with an example embodiment of a distally expanding facet implant with integrated plate and delivery device.

FIG. 13B is a partial perspective view of the distal end of the shaft of a screwdriver adapted for passage through the shaft of the holding sheath of FIG. 13A in accordance with an example embodiment of a distally expanding facet implant with integrated plate and delivery device.

FIG. 13C is a partial perspective view of the distal end of the implant holding sheath of FIG. 13A with the holding sheath illustrated partially transparent to show the distal end of the screwdriver shaft of FIG. 13B within the holding sheath and with the holding sheath and screwdriver aligned to engage the drive screw of a facet implant in accordance with an example embodiment of a distally expanding facet implant with integrated plate and delivery device.

FIG. 13D is a partial perspective view of the distal end of the implant holding sheath of FIG. 13A with the holding sheath illustrated partially transparent to show the distal end of the screwdriver shaft of FIG. 13B within the holding sheath and engaging the head of a drive screw of a facet implant and with holding arms of the implant holding sheath engaging the plates of the facet implant in accordance with an example embodiment of a distally expanding facet implant with integrated plate and delivery device.

FIG. 17 is a partial side view of the facet implant with facet implant screw and interfacet plate assembled as shown in FIG. 15 with the implant held by an implant-screwdriver holding sheath assembly with the diverting nut of the implant and the implant holding sheath illustrated in longitudinal cross-section to reveal the interior details in accordance with an example embodiment of a distally expanding facet implant with integrated plate and delivery device.

FIG. 18 is a perspective lateral view of the outline of two adjacent vertebrae of a cervical spine showing the intervertebral facet joints and disc.

FIG. 19A is a top plan view showing a chisel device illustrated partially in cross-section to show an internal guide pin track in accordance with an example embodiment of a distally expanding facet implant with integrated plate and delivery device.

FIG. 19B is a lateral view of the chisel device of FIG. 19A illustrated partially in cross-section to show the internal guide pin track in accordance with an example embodiment of a distally expanding facet implant with integrated plate and delivery device.

FIG. 19C is a proximal end view of the chisel device of FIG. 19A in accordance with an example embodiment of a distally expanding facet implant with integrated plate and delivery device.

FIG. 20A is a top plan view showing a rasp device illustrated partially in cross-section to show an internal guide pin track in accordance with an example embodiment of a distally expanding facet implant with integrated plate and delivery device.

FIG. 20B is a partial lateral view of the rasp device of FIG. 20A illustrated partially in cross-section to show the internal guide pin track in accordance with an example embodiment of a distally expanding facet implant with integrated plate and delivery device.

FIG. 20C is a proximal end view of the rasp device of FIG. 20A in accordance with an example embodiment of a distally expanding facet implant with integrated plate and delivery device.

FIG. 21A is a top plan view showing a facet guide plate in accordance with an example embodiment of a distally expanding facet implant with integrated plate and delivery device.

FIG. 21B is a lateral view of the facet guide plate of FIG. 21A in accordance with an example embodiment of a distally expanding facet implant with integrated plate and delivery device.

FIG. 21C is a partial lateral view of the facet guide plate of FIG. 21A illustrated partially in cross-section to show a pivotable facet stop lever mechanism in accordance with an example embodiment of a distally expanding facet implant with integrated plate and delivery device.

FIG. 21D is a transverse cross-sectional view of the facet guide plate of FIG. 21C in accordance with an example embodiment of a distally expanding facet implant with integrated plate and delivery device.

FIG. 22A is a lateral view of a dilator in longitudinal cross-section in accordance with an example embodiment of a distally expanding facet implant with integrated plate and delivery device.

FIG. 22B is a transverse cross-sectional view of different sizes of the dilator of FIG. 22A in accordance with an example embodiment of a distally expanding facet implant with integrated plate and delivery device.

FIG. 22C is a distal end view of the dilator of FIG. 22A in accordance with an example embodiment of a distally expanding facet implant with integrated plate and delivery device.

FIG. 22D is a partial top plan view of the distal end of the dilator of FIG. 22A in accordance with an example embodiment of a distally expanding facet implant with integrated plate and delivery device.

FIG. 23 is a side perspective view showing an introducer sheath in accordance with an example embodiment of a distally expanding facet implant with integrated plate and delivery device.

FIG. 24A is a lateral view showing a drill guide illustrated partially in longitudinal cross-section in accordance with an example embodiment of a distally expanding facet implant with integrated plate and delivery device.

DETAILED DESCRIPTION

A. Overview

Figure 1:
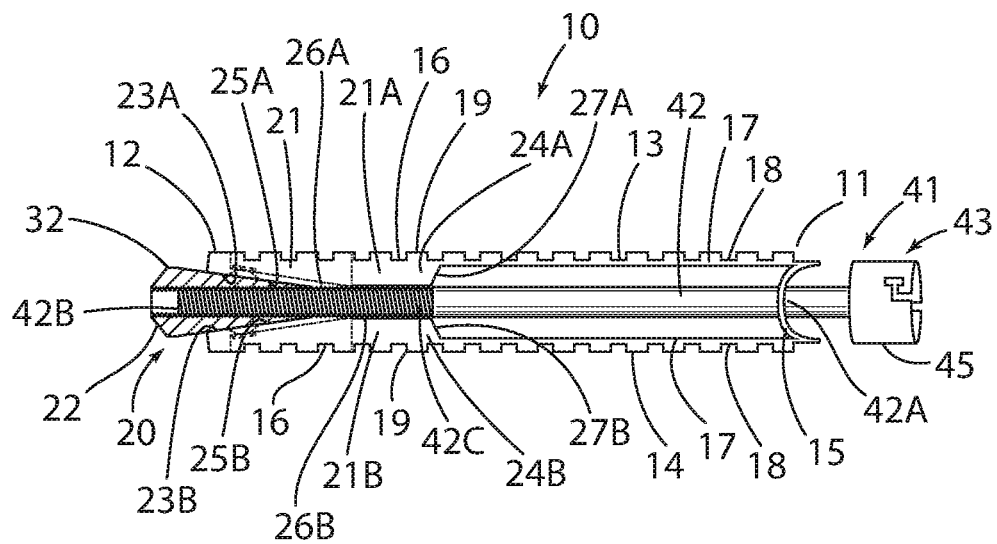
FIG. 1 is a cross-sectional side view showing a facet implant with facet implant screw and facet implant plates in non-diverted positions in accordance with an example embodiment of a distally expanding facet implant with integrated plate and delivery device.

An example distally expanding facet implant with integrated plate and delivery device generally comprises in one aspect a facet implant comprising two parallel elongated opposing rectangular plates. The plates are attached to each other at and near their respective proximal ends and are unattached at their respective distal ends. Extending longitudinally between the plates is an elongated drive screw. The proximal end of the screw includes a head that is adapted to be engaged by a screwdriver to rotate the screw. The distal end of the screw is adapted to be coupled with a diverting member positioned between the distal ends of the plates. The diverting member includes a stationary component attached to the plates and a moveable component adapted to engage the stationary component. In one embodiment, the moveable component may comprise a diverting nut having an angled engagement surface. The stationary component may include a complementarily-shaped engagement surface. When the implant is inserted in a facet joint of the cervical spine and the drive screw is rotated to tighten it relative to the diverting member, the moveable component of the diverting member is caused to move toward the proximal ends of the plates. The engagement surface of the moveable component slidingly engages the corresponding engagement surface of the stationary component and causes the distal ends of the plates to divert away from each other without causing any substantial diversion of the proximal ends of the plates. This in turn causes distraction of the distal or anterior aspect of the facet joint and widening of the intervertebral space and foramina without distracting the proximal or posterior aspect of the facet joint. The resulting effect is to maintain or restore the natural lordosis of the cervical spine and at the same time to avoid inducing kyphosis.

In another aspect, an inter-facet plate is integrated with the facet implant to assist in stabilizing the implant in the affected facet joint while preventing posterior distraction of the facet joint and locking the posterior facets of the adjacent vertebrae together. The inter-facet plate is oriented relative to the facet implant so that when the facet implant is in the facet joint the inter-facet plate abuts the external facet surfaces of the adjacent vertebrae. The inter-facet plate includes facet pins for insertion in bores drilled in the posterior facets of the adjacent vertebrae and anchor teeth to engage the posterior external facet surfaces of the vertebrae. When the drive screw is rotated to cause the distal ends of the plates of the facet implant to divert, the facet pins are caused to securely imbed in the bores locking the posterior facets together, stabilizing the implant in the facet joint, and preventing distraction of the facet joint posteriorly. The combined action of the distally expanding facet implant and the integrated inter-facet plate thus promote distraction of the anterior aspect of the facet joint, prevent distraction of the posterior aspect of the facet joint, and lock the posterior external facet surfaces of the adjacent vertebrae together resulting in a more natural lordotic position of the cervical spine.

In yet another aspect, an elongated facet implant-screwdriver holding sheath assembly is configured and adapted to hold the facet implant, drive screw, and screwdriver in an operative arrangement during insertion of the facet implant in the affected facet joint and rotation of the drive screw to distract the joint. The assembly has a distal end with mounting arms adapted to engage and hold the edges of the plates of the implant. The assembly has a proximal end from which a handle of the screwdriver can extend. An elongated shank of the screwdriver extends from the proximal end to the distal end where a drive head of the screwdriver can be caused to selectively engage and disengage with the head of the drive screw. A spring simultaneously urges the mounting arms into engagement with the facet implant and the screwdriver drive head out of engagement with the head of the drive screw. The screwdriver can be selectively repositioned against the force of the spring to bring the drive head into engagement with the head of the drive screw to rotate the screw. The screwdriver also can be selectively repositioned to move the drive head out of engagement with the head of the drive screw and to disengage the screwdriver from the screw for removal of the assembly.

In still another aspect, a mechanism for preparing the affected facet joint and delivering the facet implant to it includes several devices and components. A chisel device includes a central track for sliding over a guide pin or wire inserted in the facet joint. The chisel device can be manipulated to help remove tissue within the facet joint and open the joint up to receive the facet implant. A rasp device similarly includes a central track for sliding over the guide pin or wire into the facet joint to scrape and clean the boney surfaces of the joint prior to insertion of the facet implant. A facet guide plate also can be inserted over the guide pin or wire into the facet joint to guide various other tools to and into the facet joint. The facet guide plate includes an integrated pivoting facet stop that functions to control the distance the guide plate can be inserted within the facet joint to prevent excessive insertion. A series of dilators of different sizes can be slid successively over the facet guide to progressively dilate a passage from the epidermis to the facet joint to facilitate delivery of tools and components to the facet joint using a minimally invasive surgical approach. A drill guide can be inserted over the facet guide and delivered to the external surface of the facet joint. The drill guide is adapted to guide drill bits to specific selected points on the external facet surfaces of the adjacent vertebrae. Boreholes are drilled in the upper and lower facets to receive the facet pins of the inter-facet plate. An introducer sheath is inserted over the drill guide and the drill guide is removed. The facet implant is introduced through the introducer sheath mounted on the implant-screwdriver holding sheath assembly and is inserted inside the facet joint with the inter-facet plate abutting the external facet surfaces of the adjacent vertebrae.

Following insertion of the facet implant, the screwdriver is manipulated to tighten the drive screw. The screwdriver is then disengaged from the drive screw and the introducer sheath and implant-screwdriver holding sheath assembly are removed leaving the facet implant, drive screw, and inter-facet plate in place.

B. Facet Implant

1. Plates

Referring primarily to FIG. 1, in accordance with an example embodiment a facet implant 10 comprises an elongated structure having a proximal end 11 and a distal end 12 along a longitudinal axis with two substantially parallel, opposing, substantially planar upper and lower plates 13, 14. Each of the plates 13, 14 has an inner surface 17 and an outer surface 18. The upper and lower plates 13, 14 are interconnected at or near their respective proximal ends by an inwardly curved semi-rigid connecting sheet 15. The connecting sheet extends between the inner surfaces 17 of the plates 13, 14 preferably across their entire width and has a small central opening to allow snug passage of a drive screw described in detail below. The connecting sheet 15 allows the proximal portions of the plates 13, 14 to compress relative to each other, but prevents the proximal portions of the plates from diverting away from each other when the distal ends 12 of the plates are diverted away from each other as described in detail below. It also helps prevent lateral movement of the plates relative to each other and provides lateral stability to the implant when in use. Persons skilled in the art will appreciate that this arrangement facilitates the facet implant 10 functioning to maintain or restore the cervical spine's natural lordosis and to avoid inducing kyphosis.

In a preferred embodiment, each outer surface 18 has a plurality of rugged protruding ridges 19. The ridges 19 can be arranged substantially transversely across the outer surface 18 in relation to the longitudinal axis of the facet implant. The ridges 19 also may be arranged to slant away from the distal end 12 of the facet implant and toward the proximal end 11. Alternatively, multiple small protrusions of different shapes and sizes can be employed. Also in a preferred embodiment, each of the plates 13, 14 has multiple slots 16, which may be of various sizes and shapes, between the ridges 19. The configuration of the ridges and slots between them helps in affixing the facet implant 10 within a facet joint once inserted and minimizes movement of the facet implant in the facet joint. The preferred configuration also enhances integration or fusion of the facet implant 10 with the bones of the facet joint. The slots 16 may alternatively be formed as perforations, windows, or depressions, provided they are capable of providing the same functionality. The alternating ridges 19 and slots 16 may, and preferably do, extend substantially the entire length of the plates 13, 14. However, depending on the needs of the particular application they may be made to extend only part way.

Preferably, the plates 13, 14 are constructed of a hard, durable material, preferably metal, such as a titanium alloy. The plates also are made relatively thin to permit the distal ends 12 to be diverted by application of a reasonable amount of force but thick enough to resist substantial deformation from forces exerted on them by the vertebrae of the cervical spine. The plates should be made of a material and should be constructed so as to return substantially to their initial non-diverted position when the diverting force is removed to facilitate removal if necessary. The connecting sheet 15 is preferably constructed of similar material and with similar properties to the plates except it is preferred that the connecting sheet be somewhat more flexible than the plates 13, 14.

2. Diverting Member

Also referring primarily to FIG. 1, in accordance with an example embodiment the facet implant 10 also comprises a diverting member 20. The diverting member 20 has a stationary portion connected to the opposing plates 13, 14 at or near their respective distal ends 12, and a moveable portion that is moveable relative to and in engagement with the stationary portion to cause the distal ends 12 of the plates 13, 14 to divert away from each other. In a preferred embodiment, the stationary portion comprises a fixed diverting mass 21 and the moveable portion comprises a diverting nut 22.

The diverting mass 21 is attached or connected to the opposing inner surfaces 17 of the plates 13, 14. The diverting mass 21 has a first portion 21A connected to and extending inwardly from the inner surface 17 of the upper plate 13 and a second portion 21B connected to and extending inwardly from the opposing inner surface 17 of the lower plate 14. Each of the diverting mass portions 21A and 21B preferably has at least a portion with a relatively greater thickness dimension than the planar plate 13, 14 to which it is attached. The diverting mass portions 21A and 21B are preferably positioned in opposition to each other, with only a small opening between them through which the shaft of a drive screw described below may pass. Each of the first and second diverting mass portions 21A, 21B has a respective distal end 23A, 23B and a respective proximal end 24A, 24B. The distal end 23A, 23B preferably is located at or near the distal end 12 of the corresponding plate 13, 14 to which the corresponding diverting mass portion 21A, 21B is attached. The respective proximal end 24A, 24B preferably is located nearer to the proximal end 11 of the corresponding plate 13, 14. The diverting mass 21 thus occupies a portion of the total longitudinal distance between the distal 12 and proximal 11 ends of the opposing plates 13, 14. The diverting mass 21 may extend longitudinally from near or at the respective distal ends 12 of the plates 13, 14 for a selected distance toward the respective proximal ends 11 of the plates. The longitudinal distance the diverting mass 21 extends can vary depending on the overall dimension and other configuration and functional details of the facet implant 10.

The diverting mass 21 can be constructed in different shapes and sizes. The dimensions and shapes of the first and second portions 21A, 21B of the diverting mass 21 are selected to facilitate causing the respective plates 13, 14 to divert away from each other at and near their distal ends 12 when the diverting nut 22, which is interposed between the first and second portions, is caused to move relative to and in engagement with them as described in detail below. In a preferred embodiment, each of the first and second portions 21A, 21B is shaped such that its respective distal end 23A, 23B substantially merges into the inner surface 17 of its respective plate 13, 14 at or near the distal end 12 of the plate and slopes inwardly from that point at an angle and for a longitudinal distance toward the proximal end 11 of the plate to define an oblique engagement surface 25A, 25B. The oblique engagement surface 25A, 25B merges into a substantially flat surface or plateau 26A, 26B that continues to extend longitudinally toward the proximal end 11 of the plate for a distance before substantially merging back into the inner surface 17 of the respective plate 13, 14 at a relatively steep angle. The steeply angled opposing proximal ends 24A, 24B thus define relatively steeply angled guide surface portions 27A, 27B that facilitate insertion and retention of a distraction drive screw as described in detail below.

The diverting mass 21 can be constructed as a completely solid structure or as a cage-like structure with multiple hollow cavities. Preferably it is constructed of a hard, durable material similar to the plates 13, 14, such as a titanium alloy. It may be constructed as a separate structure and attached or connected to the plates, or may be formed integrally with the plates. In alternative embodiments, it can be formed in various other shapes and with various other structures and dimensions consistent with the function of cooperating with a moveable element, such as the diverting nut 22, to selectively divert the plates 13, 14 away from each other at and near their respective distal ends. For example, the dimensions and angles of the sloped surfaces may be modified, non-linear surfaces may be employed, and the first and second portions 21A, 21B may have different shapes to further control and customize the diversion of the individual distal ends 12 of the respective plates 13, 14 with respect to each other.

Referring primarily to FIGS. 1, 2A-2C, and 3A-3B, and as indicated above, in accordance with an example embodiment, the diverting member 20 of the facet implant 10 also comprises a moveable element in the form of a diverting nut 22. The diverting nut 22 is preferably constructed of the same type of material as the plates 13, 14 and diverting mass 21, such as a titanium alloy. The diverting nut 22 is moveable relative to and in engagement with the stationary portion of the diverting member, i.e., the diverting mass 21, to cause the plates 13, 14 to divert away from each other at and near the respective distal ends 12 without the proximal ends 11 diverting. The diverting nut 22 is interposed between the distal ends 12 of the opposing plates 13, 14 and is moveable longitudinally between them in a manner described in detail below.

In a preferred embodiment, the diverting nut 22 comprises an elongated solid nut having a proximal member 28 with a proximal tip 29, a distal member 30 with a distal tip 31, and a plateau member 32 connecting the distal and proximal members. Viewed longitudinally from the distal tip 31, the diverting nut is shaped generally as an irregular hexagon having substantially parallel wider top and bottom surfaces with corresponding lateral edges joined by relatively short obtusely-angled side surface segments. Viewed from the side, the diverting nut has an elongated substantially fusiform profile with the proximal member 28 having a substantially greater longitudinal dimension than the distal member 30. The distal member 30 extends distally from the plateau member 32 at a relatively steep angle to an acutely-angled distal tip 31. The proximal member 28 extends proximally from the plateau member 32 for a relatively longer distance than the distal member and at a relatively shallower angle to an acutely-angled proximal tip 29. The distal tip 31 also is relatively wider than the proximal tip 29. An internal screw tract 33 (illustrated by dotted lines in FIG. 2A) traverses the center of the diverting nut 22 along its entire longitudinal axis starting at the proximal tip 29 and extending through the distal tip 31.

Figure 2A:
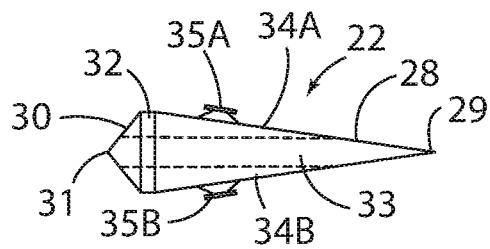
FIG. 2A is a side view showing a diverting nut of a facet implant in accordance with an example embodiment of a distally expanding facet implant with integrated plate and delivery device.
Figure 2B:
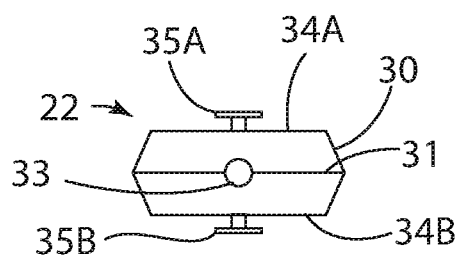
FIG. 2B is a distal end view of the diverting nut of FIG. 2A in accordance with an example embodiment of a distally expanding facet implant with integrated plate and delivery device.
Figure 2C:
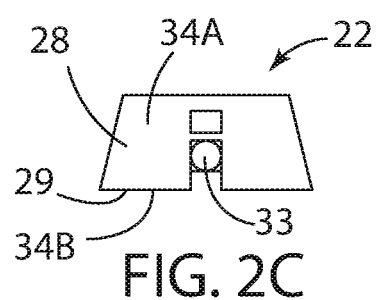
FIG. 2C is a proximal end view of the diverting nut of FIG. 2A in accordance with an example embodiment of a distally expanding facet implant with integrated plate and delivery device.
Figure 3A:
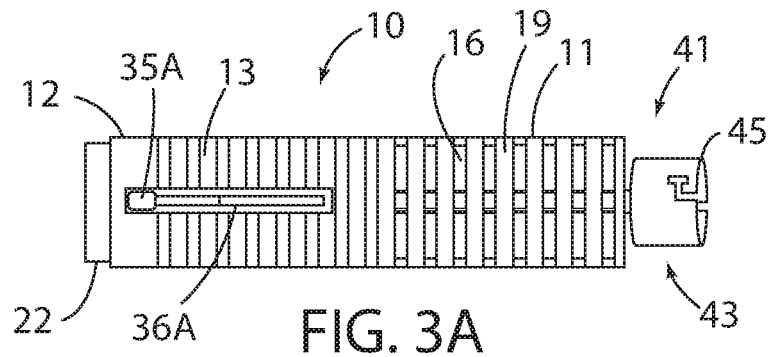
FIG. 3A is a top plan view of a facet implant in accordance with an example embodiment of a distally expanding facet implant with integrated plate and delivery device.
Figure 3B:
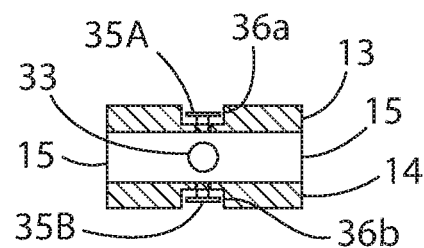
FIG. 3B is a transverse cross-sectional view of the distal end of the facet implant of FIG. 3A in accordance with an example embodiment of a distally expanding facet implant with integrated plate and delivery device.

It is noted that the diverting nut 22 is illustrated in FIG. 1 (and also FIGS. 5, 14, 15, and 17) in cross-section to better demonstrate the interconnection between and relative positions of the nut and the shaft of the drive screw described in detail below. However, in a preferred embodiment the diverting nut is a solid structure, as illustrated in FIGS. 2A-2C and described above, and the portion of the screw extending within the diverting nut 22 would not be visible.

In alternative embodiments, the distal and proximal members and tips of the diverting nut 22 can be curved or rounded to achieve the same function of moveably engaging the diverting mass 21 to cause the plates 13, 14 to divert away from each other at and near the distal ends 12. Alternatively or in addition, the diverting nut 22 can be constructed in various shapes and structures, including a cage-like configuration, that achieve the same function of moveably engaging the diverting mass.

The proximal member 28 defines a pair of relatively wide and long upper and lower tapered surfaces 34A, 34B that extend from the plateau member 32 proximally to the proximal tip 29. Mounted on each surface 34A, 34B is a substantially T-shaped fin structure 35A, 35B. The fins are adapted to be retained within and to slide along elongated fin tracks 36A, 36B in the upper and lower plates 13, 14 of the facet implant 10 when the diverting nut 22 moves along the longitudinal axis of the facet implant between the plates as described below.

Figure 4:
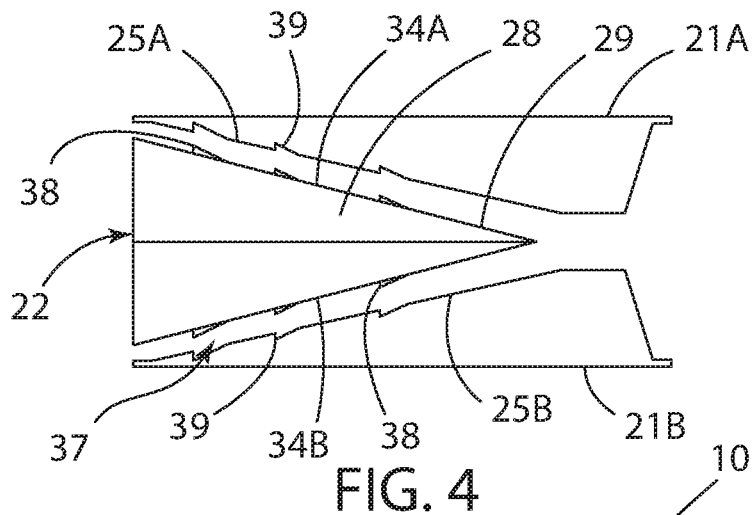
FIG. 4 is a partial longitudinal cross-sectional view showing a diverting nut and diverting mass locking interface of a facet implant in accordance with an example embodiment of a distally expanding facet implant with integrated plate and delivery device.
Figure 5:
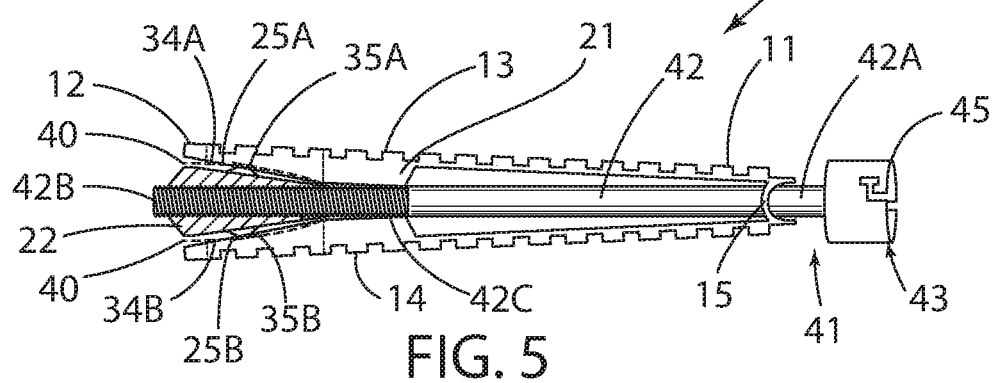
FIG. 5 is a side view showing a facet implant with a facet implant screw, diverting nut (illustrated in cross-section), and facet implant plates in a diverted position in accordance with an example embodiment of a distally expanding facet implant with integrated plate and delivery device.
Figure 6:
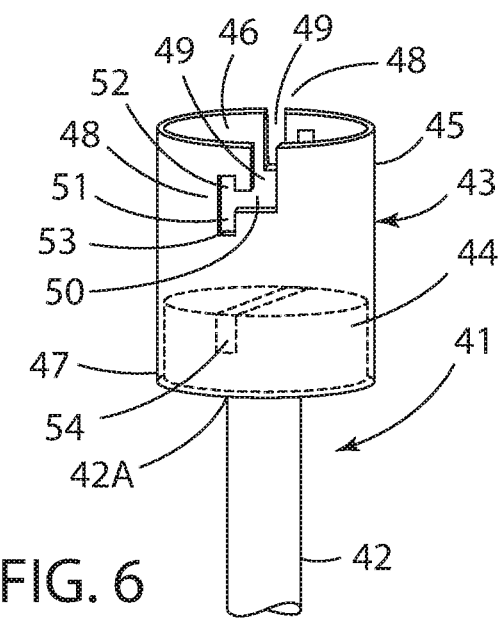
FIG. 6 is a perspective view of the head of a facet implant screw of a facet implant shown partially transparent to reveal the interior of the head in accordance with an example embodiment of a distally expanding facet implant with integrated plate and delivery device.
Figure 7A:
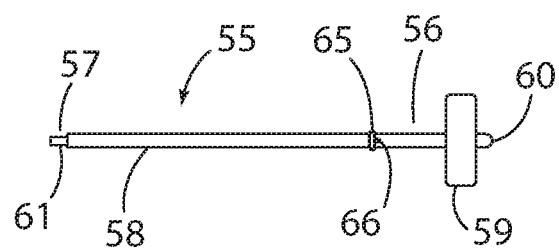
FIG. 7A is a side view of a screwdriver for use with a facet implant screw of a facet implant in accordance with an example embodiment of a distally expanding facet implant with integrated plate and delivery device.
Figure 7B:
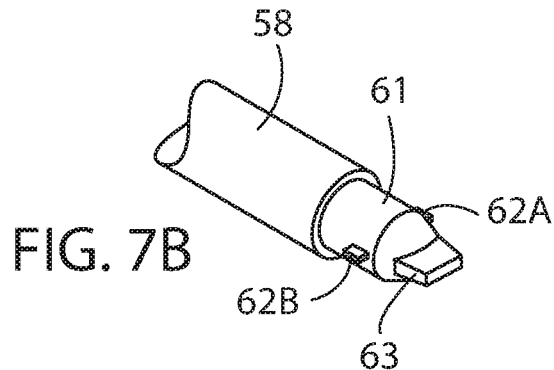
FIG. 7B is a partial top plan view of the distal end of the screwdriver of FIG. 7A in accordance with an example embodiment of a distally expanding facet implant with integrated plate and delivery device.
Figure 7C:
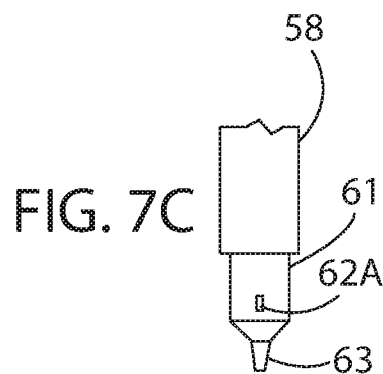
FIG. 7C is a partial lateral view of the distal end of the screwdriver of FIG. 7B in accordance with an example embodiment of a distally expanding facet implant with integrated plate and delivery device.
Figure 7D:
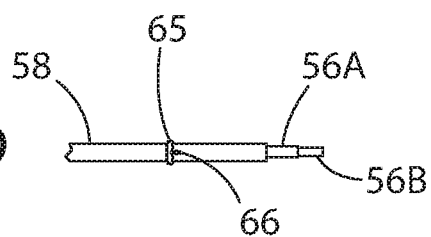
FIG. 7D is a partial side view of the proximal end of the screwdriver of FIG. 7A with a handle of the screwdriver removed in accordance with an example embodiment of a distally expanding facet implant with integrated plate and delivery device.
Figure 7E:
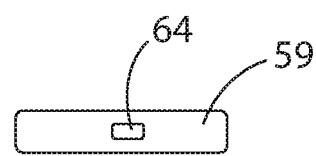
FIG. 7E is a top view of the removed handle of the screwdriver of FIG. 7A in accordance with an example embodiment of a distally expanding facet implant with integrated plate and delivery device.
Figure 7F:
FIG. 7F is a cross-sectional side view of a handle cap of the screwdriver of FIG. 7A detached from the screwdriver in accordance with an example embodiment of a distally expanding facet implant with integrated plate and delivery device.
Figure 8A:
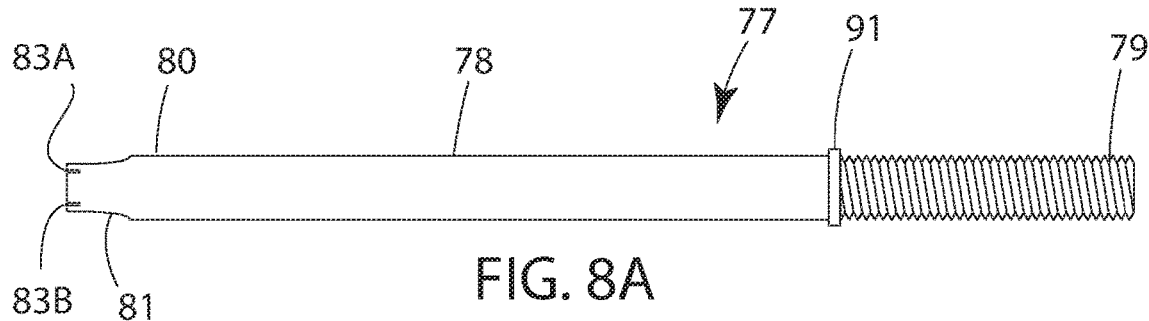
FIG. 8A is a lateral view of an implant holding sheath in accordance with an example embodiment of a distally expanding facet implant with integrated plate and delivery device.
Figure 8B:
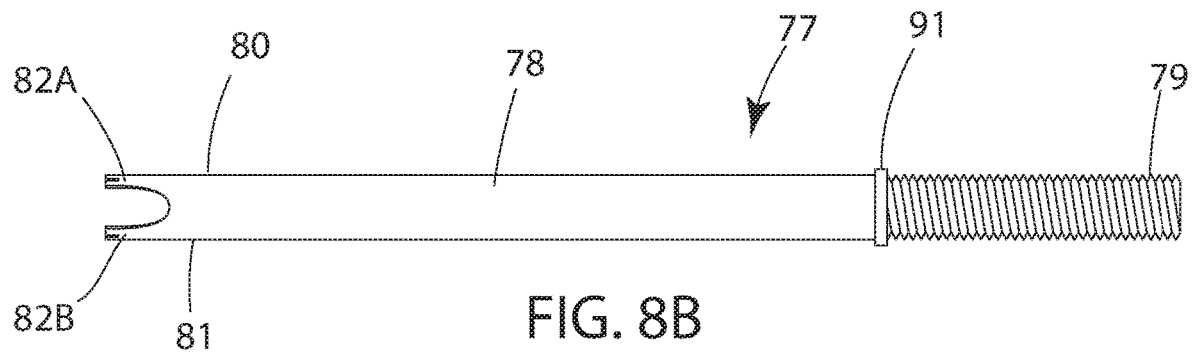
FIG. 8B is a top plan of the implant holding sheath of FIG. 8A in accordance with an example embodiment of a distally expanding facet implant with integrated plate and delivery device.
Figure 9:
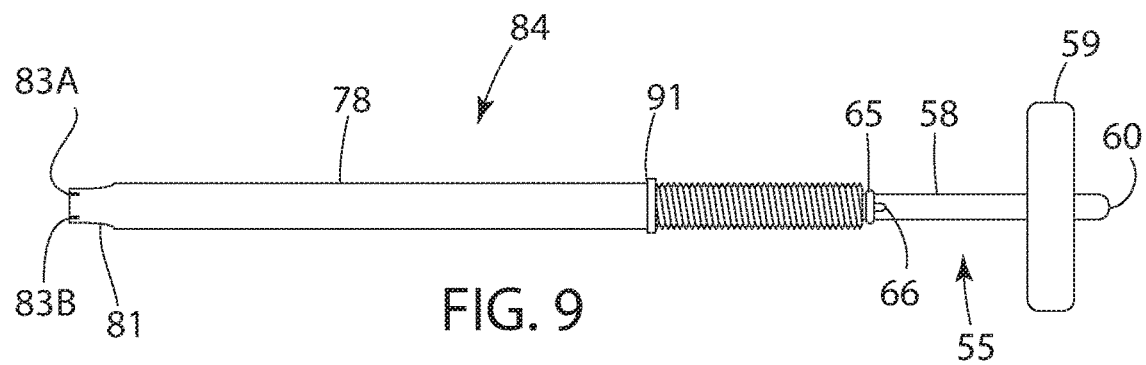
FIG. 9 is a lateral view showing an implant-screwdriver holding sheath assembly in accordance with an example embodiment of a distally expanding facet implant with integrated plate and delivery device.
Figure 10:
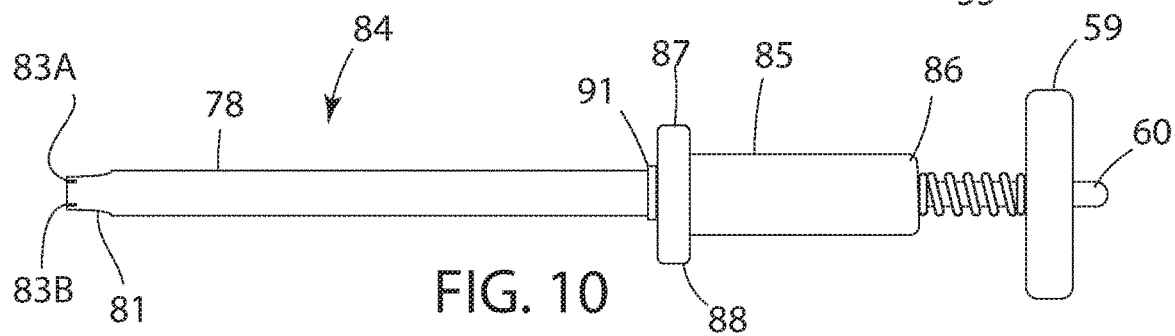
FIG. 10 is a lateral view of the implant-screwdriver holding sheath assembly of FIG. 9 with an assembly handle and spring mounted in accordance with an example embodiment of a distally expanding facet implant with integrated plate and delivery device.

Referring primarily to FIGS. 1, 4 and 5, the diverting nut 22 initially assumes the position shown in FIG. 1 interposed between the upper and lower plates 13, 14 of the facet implant 10. When the diverting nut 22 is caused to move along the longitudinal axis of the facet implant 10 toward the proximal end 11, as shown in FIG. 5, the tapered surfaces 34A, 34B of the proximal member 28 slide under and moveably engage the stationary oblique engagement surfaces 25A, 25B of the first and second portions 21A, 21B of the diverting mass 21 between the plates 13, 14 pushing them away from each other and expanding the implant distal end 12.

As the diverting nut 22 moves along the longitudinal axis of the facet implant 10, the T-shaped fins 35A, 35B protruding from the tapered surfaces 34A, 34B of the proximal member 28 of the diverting nut 22 slide in the fin tracks 36A, 36B of the opposing upper and lower plates 13, 14. This stabilizes the diverting nut 22 while sliding within the facet implant 10 and also resists unintentional diversion of the distal ends 12 of the plates, 13, 14, which facilitates the process of inserting the facet implant into the facet joint. Although the fins are described as being substantially T-shaped, in alternative embodiments they can take different shapes and be connected with the diverting nut 22 in different manners consistent with providing the foregoing functions.

The diverting member 20 can be provided optionally with a stop or lock mechanism 37 in accordance with one embodiment. The stop mechanism 37 prevents the moveable element of the diverting member 20, i.e., the diverting nut 22, from moving distally relative to the stationary element of the diverting member, i.e., the diverting mass 21. More particularly, the stop mechanism 37 functions to prevent the tapered surfaces 34A, 34B of the proximal member 28 of the diverting nut 22 from moving distally with respect to the stationary oblique engagement surfaces 25A, 25B of the first and second portions 21A, 21B of the diverting mass 21 as they slide under and engage those surfaces in the proximal direction to divert the distal ends 12 of the plates 13, 14. In one embodiment, the stop mechanism 37 comprises multiple stop ridges 38 protruding from the tapered surfaces 34A, 34B of the moveable diverting nut 22 and corresponding grooves 39 in the oblique engagement surfaces 25A, 25B of the stationary diverting mass 21. The ridges 38 and grooves 39 can be arranged in various configurations but are preferably arranged transversely across the respective opposing surfaces 25A, 25B, 34A, 34B of the diverting nut 22 and diverting mass 21. Also in a preferred embodiment, the stop ridges 38 are in the form of right-angled triangles that are tapered toward the proximal ends of the opposing surfaces and the grooves are correspondingly shaped. This configuration facilitates sliding movement of the diverting nut 22 in the direction of the proximal end 11 of the facet implant while preventing its movement toward the distal end 12.

If subsequent adjustment or removal of the facet implant is anticipated or desired, the stop or lock mechanism 37 may be omitted. The tapered surfaces 34A, 34B of the proximal member 28 of the diverting nut 22 then may be permitted, when desired, to slide distally under and in engagement with the stationary oblique engagement surfaces 25A, 25B of the first and second portions 21A, 21B of the diverting mass 21 to release the distal ends 12 of the plates 13, 14 from a diverted state back toward a non-diverted state by loosening a drive screw as described below. Alternatively, the stop ridges 38 of the moveable diverting nut 22 and corresponding grooves 39 of the stationary diverting mass 21 may be made relatively shallow to create resistance to distal movement of the nut while not completely preventing it. In another alternative, the stop ridges 38 and grooves 39 can be rounded or have other corresponding shapes that resist but do not completely prevent distal movement of the diverting nut. In yet another alternative, the opposing surfaces 25A, 25B, 34A, 34B of the diverting nut and diverting mass instead can be roughened to resist rather than fully prevent distal movement of the nut. In these alternatives, distal movement of the nut is generally resisted, but loosening of the drive screw by a certain amount results in releasing the distal ends of the plates back toward the non-diverted state.

As described above, as the diverting nut 22 moves proximally along the longitudinal axis of the facet implant 10, the diverting member 20 diverts the plates 13, 14 at and near their respective distal ends 12. Due to the natural pressure exerted by the adjacent vertebrae and the bony boundaries of the intervertebral facet joint, the respective proximal ends 11 of the plates 13, 14 are likely to converge somewhat while the distal ends 12 divert to expand the facet implant 10. As best seen in FIG. 5, in reality the actual expanded shapes of the distal ends 12 likely will take a slightly curved shape as shown by dotted lines 40 due to squeezing pressure from the bony boundaries of the vertebrae adjacent the joint. However, this does not adversely affect the functionality of the facet implant 10.

3. Drive Screw

Referring primarily to FIGS. 1, 3A, and 5-6, in accordance with an example embodiment the facet implant 10 also comprises an elongated drive screw 41. The drive screw 41 is adapted to be coupled with the moveable diverting nut 22 of the diverting member 20 and is operable with the diverting nut to cause the opposing plates 13, 14 of the facet implant 10 to divert away from each other at and near the distal end 12 of the facet implant after it is inserted into the facet joint as described in detail below. The drive screw 41 is preferably constructed of a similar material to the other components of the facet implant, such as a titanium alloy.

The drive screw 41 comprises an elongated shaft 42 having a proximal end 42A, a distal end 42B, and a head 43 attached or integrally formed at the proximal end. With the screw 41 coupled with the diverting nut 22, the head 43 is ideally located just proximal to the proximal end 11 of the facet implant 10. The shaft 42 traverses the entire length of the facet implant 10 along its longitudinal axis through the connecting sheet 15, between the opposing upper and lower plates 13, 14 and between the diverting mass portions 21A, 21B. The proximal end 42A protrudes slightly from the proximal end 11 of the facet implant and the distal end 42B extends into the proximal end of the diverting nut 22 at the distal end 12 of the facet implant. In use of the implant, the distal end 42B may extend partially or completely through the diverting nut 22. Compare FIGS. 1, 5, 14 and 15. At least a portion of the shaft 42 is adapted to be coupled with the diverting nut 22 and is threaded to engage corresponding threads in the screw tract 33 of the diverting nut. An intermediate portion 42C of the shaft 42 between the proximal 42A and distal 42B ends extends through the opening between the interior flat plateau surfaces 26A, 26B of the diverting mass 21, which acts both as a guide for the shaft 42 and to help stabilize it when the screw 41 is being rotated to pull the diverting nut 22 proximally as described below.

The head 43 of the screw 41 comprises a solid base 44 with a hollow crown 45 extending outward proximally therefrom. The crown 45 has an open proximal end 46 and a distal end 47 that is attached to or integrally formed with the solid base 44. In one example of the embodiment the solid base 44 and hollow crown 45 of the head 43 are each substantially cylindrical in shape. However, persons skilled in the art will appreciate the head 43 can take other shapes capable of achieving the functions described herein.

The crown 45 has a pair of specially-shaped slots 48 that are adapted to cooperate with guide pins 62A, 62B of a screwdriver 55 described in detail below. The slots 48 together provide a guide track, a retention mechanism, and a function selection mechanism for the screwdriver 55. The slots 48 are preferably formed as mirror images of each other in opposing sections of the cylindrical side wall of the crown 45. Each slot preferably comprises a vertical entrance slot member 49, a horizontal connecting slot member 50, and a vertical function selection slot member 51. The entrance slot member 49 extends vertically from the open proximal end of 46 of the crown toward the distal end 47 of the crown until it perpendicularly intersects one end of the horizontal connecting slot member 50. The other end of the horizontal connecting slot member 50 in turn perpendicularly intersects the vertical function selection slot member 51 medially between a proximal end 52 and a distal end 53. As will become clear, the proximal end 52 corresponds to a screw pulling function position of the screwdriver and the distal end 53 corresponds to a screw rotation function position of the screwdriver.

A drive slot 54 is formed in the solid base 44 of the screw head 43. The drive slot 54 functions to engage a correspondingly-shaped drive head 63 of the screwdriver 55 adapted to be used with the screw 41 as described below. The drive slot 54 is positioned in the solid base 44 such that when guide pins 62A, 62B of the screwdriver are positioned in the screwing function position 53 of the vertical function selection slot member 51 of the crown 45, a drive head 63 of the screwdriver is aligned with and in engagement with the drive slot 54. In one embodiment shown in FIG. 6, the drive slot extends transversely across the diameter of the solid base 44 and is configured to engage a flat drive head of the screwdriver. In alternative embodiments, the drive slot 54 can have various different configurations and engage various different corresponding-shaped drive heads, provided an alternative configuration permits the screwdriver 55 to be adequately engaged with the screw 41 so that when the screwdriver is rotated the screw is caused to rotate. For example, the drive slot 54 can be configured to engage Phillips, star, and other drive head configurations.

In order to ensure that the drive head 63 of the screwdriver is completely seated in and engaged with the drive slot 54 of the screw head 43 when the guide pins 62A, 62B are positioned in the screwing function position 53 of the vertical function selection slot member 51, the depth of the screwing function position portion of the vertical function selection slot member 51 should equal or exceed the depth of the drive slot 54. Further, the distance between the distal end 53 of the vertical function selection slot member 51 and the bottom of the drive slot 54 should correspond to the distance between the distal end of screwdriver guide pins 62A, 62B, as further described below, and the distal end of the screwdriver drive head 63. This configuration permits the screwdriver to securely engage the screw head 43 and rotate the screw 41 when pushed in, and to pull the screw 41 proximally when the screwdriver is in the pulling function position 52 of the vertical function selection slot member 51.

From the foregoing descriptions it should be apparent to those skilled in the art that with the screw 41 coupled within the diverting nut 22 via the threads on the screw shaft 42 and inside the screw tract 33 of the diverting nut, rotation of the screw 41 causes the diverting nut 22 to move toward the proximal end 11 of the facet implant 10. The proximal ends of the plates 13, 14 with the connecting sheet 15 engage the base 44 of the screw head 43 and prevent the screw 41 from moving toward the distal end 12 of the facet implant. As the screw 41 is rotated it tightens relative to the diverting nut 22 and the threads on the shaft 42 pull in the proximal direction on the threads within the screw tract 33. The diverting nut thus is caused to move toward the proximal end 11 of the facet implant along its longitudinal axis. As the screw 41 continues to be rotated and tightened, the tapered surfaces 34A, 34B of the proximal member 28 of the diverting nut 22 engage and slide proximally relative to the corresponding oblique engagement surfaces 25A, 25B of the stationary diverting mass 21 on the interior surfaces 17 of the plates 13, 14. The more the screw 41 is tightened, the further the diverting nut 22 is pulled in the direction of the proximal end 11 of the facet implant 10. The further the diverting nut 22 is pulled proximally, the greater is the outer dimension between the sloping engagement surfaces 34A, 34B present between the corresponding engagement surfaces 25A, 25B of the stationary mass 21 on the inner surfaces 17 of the plates 13, 14. Thus, the further the diverting nut is pulled proximally between the plates 13, 14, the further the plates are caused to divert outwardly away from each other at and near the distal end 12.

As the screw is tightened, the stop ridges 38 on the surfaces 34A, 34B of the proximal member 28 of the diverting nut 22 engage the corresponding grooves 39 on the corresponding oblique engagement surfaces 25A, 25B of the stationary diverting mass 21 on the inner surfaces 17 of the plates 13, 14. This locks the diverting nut in position and prevents it from moving toward the distal end 12 of the facet implant once the screw has been tightened to divert the plates the desired amount. Alternatively, as described previously, the stop ridges and grooves may be omitted or altered so that rotating the screw in the opposite direction to loosen it allows the diverting nut to move toward the distal end of the implant and reduce the distance by which the plates are diverted.

C. Screw Driver

Referring primarily to FIGS. 7A-7F, an example embodiment of a screwdriver 55 adapted for use with the facet implant 10 is described. Screwdriver 55 has a proximal end 56 and a distal end 57 connected by an elongated rod-like shank or shaft 58. A cylindrical or cuboid handle 59 is mounted at the proximal end 56 and secured in place by a cap 60. The distal end 57 can include a tapered or relatively narrowed portion 61. The tapered or narrowed portion 61 can include one or preferably a pair of screwdriver guide pins 62A, 62B. The guide pins are configured and adapted to engage with the specially-shaped slots 48 in the crown 45 of the screw head 43 of drive screw 41 to allow the screwdriver 55 to selectively engage and rotate the drive screw 41 or to pull it in the direction of the proximal end 11 of the facet implant 10. The guide pins 62A, 62B protrude substantially perpendicularly from the tapered or narrowed portion 61 and are located on opposite sides thereof corresponding to the locations of the slots 48 in the crown 45. As described above, the guide pins 62A, 62B are also spaced proximally from the distal tip of the screwdriver by a distance corresponding to the distance between the distal end 53 of the vertical function selection slot member 51 in the crown 45 and the bottom of the drive slot 54 in the screw head 43.

The distal tip of the narrowed portion 61 comprises an elongated cuboidal drive head 63 that is configured and adapted to be fully seated in and to engage the drive slot 54 in the head 43 of screw 41. In the embodiment illustrated, the drive head 63 is similar to the tip of a flat blade screwdriver. As described above, however, in alternative embodiments the drive head 63 and corresponding drive slot 54 can be of various other shapes that are suitable to achieve the function of the screwdriver 55 engaging the head 43 of the drive screw 41 to rotate the screw and divert the distal ends 12 of the plates 13, 14 of the facet implant 10.

The proximal end 56 of the shank 58 includes a substantially transversely elongated planar member 56A and a substantially cylindrical threaded member 56B abutting the planar member. Both are substantially coaxial with the shank 58. The screwdriver handle 59 has a mounting opening 64 that corresponds in shape to the planar member 56A and that is adapted to fit onto and over the planar member to mount the handle 59 and prevent it from rotating relative to the shank 58. Alternatively, the cross-section of the planar member 56A can be of any shape that can achieve the function of engaging the mounting opening 64 of the handle 59 to enable the screwdriver to rotate with the handle 59. The cap 60 fits onto and over the threaded member 56B to retain the handle 59 securely on the planar member 56A. The cap 60 is ideally a solid component that has a cylindrical cavity with interior threads adapted to engage with the threads of the threaded member 56B so that the handle 59 can be selectively detached from and reinserted onto the shank 58.

Located on the shank 58 near the proximal end 56 is a screwdriver stop 65. The screwdriver stop extends annularly around the shank. Attached to or formed integrally with the screwdriver stop is a pair of proximally-facing lock pins 66. Each pin of the pair is located on an opposite side of the screwdriver stop. As described in detail below, the screwdriver stop and lock pins are configured to function in cooperation with locking teeth 95 of an implant-screwdriver holding sheath assembly 84 described in detail below such that the screwdriver is selectively moveable within the assembly between the screw rotation and screw pulling positions described above.

D. Inter-Facet Plate

Figure 15:
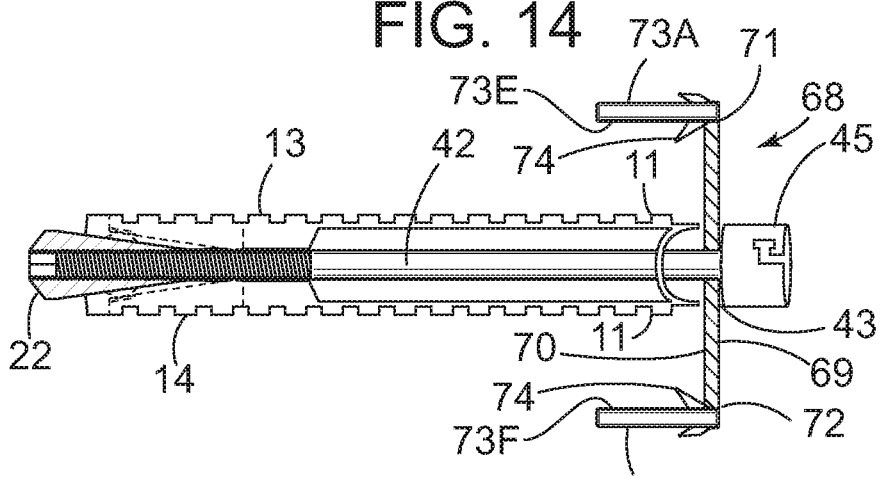
FIG. 15 is a side view of a facet implant with a facet implant screw and interfacet plate assembled with the diverting nut of the implant illustrated in cross-section in accordance with an example embodiment of a distally expanding facet implant with integrated plate and delivery device.
Figure 16:
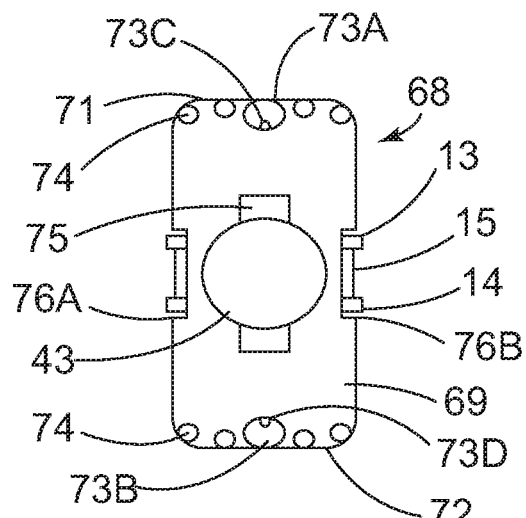
FIG. 16 is a proximal end view of the facet implant with facet implant screw and interfacet plate assembled as shown in FIG. 15 in accordance with an example embodiment of a distally expanding facet implant with integrated plate and delivery device.

Referring primarily to FIGS. 15-17, in an example embodiment, an inter-facet plate 68 can be integrated with the facet implant 10 to further stabilize a facet joint receiving the implant in the cervical spine extension position (lordosis). In a preferred embodiment, the inter-facet plate 68 comprises a substantially rectangular planar structure with a longitudinal axis. However, it is understood that the inter-facet plate can be of any shape or configuration that would achieve the same function. The inter-facet plate 68 is preferably positioned between the head 43 of screw 41 and the proximal ends 11 of the implant plates 13, 14 oriented with its longitudinal axis substantially perpendicular to the longitudinal axis of the facet implant 10 and aligned with the plates 13, 14. The inter-facet plate has an external or posterior-facing surface 69, an internal or anterior-facing surface 70, a peripheral top edge 71 above the upper plate 13, and a peripheral bottom edge 72 below the bottom plate 14.

At least one relatively long facet pin 73A, 73B protrudes internally in the anterior direction from the plate at or near each of the peripheral edges 71, 72. Preferably the facet pins 73A, 73B protrude substantially perpendicularly to the plane of the plate and directly above and below the respective plates 13, 14. Each of the facet pins 73A, 73B comprises a substantially cylindrical shaft having a base attached to the internal surface 70 of the inter-facet plate 68 and a distal free end. The free ends of the pins 73A, 73B are adapted to be inserted into boreholes in the respective facets of the upper and lower vertebrae adjacent the facet joint receiving the facet implant 10 as described in detail below. Also protruding substantially perpendicularly from the plate 68 at or near each of the peripheral edges 71, 72 are a plurality of anchoring teeth 74. The anchoring teeth 74 comprise shorter, sharp protrusions that are adapted to grip the posterior-facing surfaces of the facets and to help securely anchor the plate 68 to them when the pins 73A, 73B are inserted in the facets external surfaces 104, 105 as described below. While the anchoring teeth 74 are preferably located at or near the top and bottom peripheral edges 71, 72 of the inter-facet plate 68, in alternative embodiments they can be distributed anywhere on the internal surface 70.

The inter-facet plate 68 also includes a centrally-located screw shaft opening 75 that is adapted to allow the shaft 42 of the drive screw 41 to pass through the inter-facet plate 71 but not the head 43. In an example embodiment, screw shaft opening 75 comprises an elongated slot that has a width slightly greater than the diameter of the screw shaft 42 but less than the diameter of the head 43. Preferably the slot has a larger height dimension to permit vertical adjustment of the screw 41 and angulation of the implant in relation to the inter-facet plate 68. This configuration provides flexibility for achieving an optimal fit of the inter-facet plate to the external posterior facet surfaces of the adjacent vertebrae as described in further detail below.

In a preferred embodiment, each facet pin 73A, 73B includes a longitudinal groove 73E, 73F on a portion of its exterior surface facing the facet implant 10. The groove extends from the base of the facet pin to or near the free end of the pin. A small hole 73C, 73D extends through the plate 68 and a portion of the periphery of the base of the facet pin in alignment with the groove to form a longitudinal track for a guide pin to help guide the facet pins into bore holes in the external posterior facet surfaces of vertebrae adjacent the facet joint receiving the facet implant as described in detail below. The holes 73C, 73D and the corresponding grooves 73E, 73F can be of various transverse cross-sectional depths and shapes. Alternatively, tracks can be formed within the facet pins 73A, 73B to guide them over guide pins or wires into the boreholes.

Elongated detents 76A, 76B are formed in respective opposite lateral peripheral edges of the inter-facet plate 68. The detents are formed with their longitudinal axes substantially parallel to the longitudinal axis of the screw shaft slot 75. The detents provide passage spaces for mounting arms 82A, 82B of an implant holder 81 to pass through the inter-facet plate in order to engage the facet implant plates 13, 14 as described below.

E. Implant Delivery and Facet Joint Preparation Components

1. Implant Holding Sheath/Implant-Screwdriver Holding Sheath Assembly

Referring primarily to FIGS. 8A-8B, 9-10, 11A-11B, 12A-C, and 13, 13A-D, and 14, an example embodiment of an implant holding sheath 77 and an implant-screwdriver holding sheath assembly 84 adapted for use with the facet implant 10 are described. The holding sheath 77 comprises a tubular shaft 78 having a proximal member 79 and a distal member 80. The proximal member 79 has a threaded exterior surface that is adapted to couple the holding sheath with an assembly handle 85 to form the implant-screwdriver holding sheath assembly 84 as described in detail below. An annular stop ring 91 is attached to or integrated with the exterior surface of the tubular shaft 78 just distally of the threaded proximal member 79. The distal member 80 comprises an implant holder 81. The implant holder 81 comprises a pair of mounting arms 82A, 82B. Each mounting arm 82A, 82B has the form of a distally-extending, relatively wide fork-like tine. Each mounting arm includes a pair of slots 83A, 83B and each slot is adapted to engage with and to seat an edge of the proximal end 11 of the upper and lower plates 13, 14 of the facet implant 10. As indicated above, the mounting arms 82A, 82B are adapted to pass through the detents 76A, 76B of the inter-facet plate 68 in order to engage the plates 13, 14.

The implant-screwdriver holding sheath assembly 84 has the screwdriver 55 inserted into the tubular shaft 78 of the holding sheath 77 from its proximal end. The distance between the position of the annular screwdriver stop 65 on the screwdriver shank 58 and the screwdriver handle 59 determines the distance the drive head 63 of the screwdriver protrudes from the distal end of the shaft 78 in relation to the mounting arms 82A, 82B. The distal tip of the drive head 63 should extend far enough beyond the distal end of the shaft 78 to fully seat in and engage the drive slot 54 in the head 43 of drive screw 41 when the edges of the proximal ends 11 of the plates 13, 14 are fully seated in the slots 83A, 83B of the mounting arms 82A, 82B.

With the screwdriver handle 59 removed, the implant-screwdriver holding sheath assembly handle 85 is inserted over the screwdriver's shank 58 from its proximal end. The assembly handle 85 comprises a tubular structure preferably constructed of a plastic polymer but also is suitably constructed of other rigid materials including metals. The handle 85 has a proximal end 86 with a proximal end opening 86A and a distal end 87 with a distal end opening 87A. The proximal and distal end openings 86A, 87A are coaxial. The proximal end opening 86A has a diameter sufficient to pass over the shank 58 of the screwdriver 55 and the distal end opening 87A has a diameter sufficient for the holding sheath 77 to pass through. The distal end 87 preferably terminates in an external flange 88, which facilitates a better non-slipping grip of the implant-screwdriver holding sheath assembly 84 while in use.

The assembly handle 85 has a substantially cylindrical interior space 89 with an interior surface 90. The wall of the handle enclosing the interior space should be thick enough to provide adequate structural support and the diameter of the handle should be sufficient to provide adequate gripping surface when the implant-screwdriver sheath assembly is in use. The interior surface 90 is preferably threaded to permit the proximal member 79 of the holding sheath 77 handle to be screwed into the handle to couple them together. The stop ring 91 is positioned on the exterior surface of the threaded proximal member 79 so as to engage the distal edge of the assembly handle 85 and prevent the holding sheath 77 from being screwed into the assembly handle 85 by more than a predetermined distance or, in other words, to prevent the assembly handle from being positioned distally on the holding sheath by more than a predetermined distance.

An annular locking ring 92 is located in the interior space 89 of the assembly handle 85 just inside the proximal end opening 86A. The locking ring is preferably constructed of a metallic material but also can be constructed of other rigid materials. The annular locking ring has a central opening 93 that is dimensioned to permit a snug fit with the screwdriver shank 58 when it is inserted while still permitting the shank to be rotated. The locking ring also has an interior surface 94 with a plurality of locking teeth 95. The locking teeth are configured and adapted to engage the at least one but ideally a pair of locking pins 66 on opposite sides of the annular screwdriver stop 65 on the shank 58 of the screwdriver 55 when the screwdriver is in a released or disengaged state or position, as shown in FIG. 12A. In this state or position, the drive head 63 of the screwdriver 55 is disengaged from the drive slot 54 in the head 43 of drive screw 41 and the engagement of the locking pins 66 and locking teeth 95 prevent the screwdriver from being rotated relative to the holding sheath 77. Also in this state, the screwdriver guide pins 62A, 62B are engaged and retained in the proximal end 52 of the function selection slot member 51 in the crown 45 of the screw head 43 of screw 41, which corresponds to the screw pulling function or position of the screwdriver.

In contrast, as shown in FIG. 12B, when the shank 58 of the screwdriver 55 is pushed in toward the distal end of the assembly handle 85, the locking pins 66 disengage from the locking teeth 95. In this position, the drive head 63 of the screwdriver 55 can be moved into engagement position with the drive slot 54 in the head 43 of the drive screw 41 and the screwdriver can be rotated to rotate and tighten the screw relative to the diverting member 20. In this position, the screwdriver guide pins 62A, 62B are engaged in the distal end 53 of the function selection slot member 51 in the crown 45 of the screw head 43, which corresponds to the screw rotating function or position of the screwdriver.

From the foregoing it will be appreciated that the screwdriver 55 is selectively moveable within and relative to the implant-screwdriver holding sheath assembly 84 between a first more proximal position in which it is operable to pull the drive screw 41 and coupled diverting member 20 proximally, and a second more distal position in which it is operable to rotate the drive screw 41 to tighten or loosen it relative to the diverting member 20. The position of the screwdriver stop 65 on the shank 58 of the screwdriver and the position of the proximal end of the holding sheath 77 within the assembly handle 85 (as determined by the position of the stop ring 91 on the shaft 78 of the holding sheath) define and limit the overall range of relative movements between the screwdriver and the implant-screwdriver holding sheath assembly 84. The screwdriver stop 65 is positioned on the shank a sufficient distance distally from the proximal end 86 of the assembly handle 85 to permit the locking pins 66 to be moved into and out of engagement with the locking teeth 95 of the annular locking ring 92 and for the drive head 63 of the screwdriver 55 to be selectively moved into and out of engagement with the drive slot 54 in the head 43 of drive screw 41 without the handle 59 of the screwdriver contacting the proximal end 86 of the assembly handle 85. At the same time, the position of the annular stop ring 91 on the shaft 78 of the holding sheath 77 determines the distance the holding sheath is permitted to be inserted within the assembly handle 85. This in in turn determines the maximum distance the screwdriver 55 is permitted to move distally relative to the implant-screwdriver holding sheath assembly 84. This is because as the screwdriver moves distally the screwdriver stop 65 eventually engages the proximal end of the holding sheath 77 and further distal movement is blocked.

The implant-screwdriver holding sheath assembly 84 is assembled by first removing the handle 59 from the screwdriver 55 and sliding the assembly handle 85 onto the screwdriver shank 58 over the proximal end 56 of the shank. A spring 67, such as a coil spring, is then slid over the proximal end 56 of the shank 58 with a distal end of the spring abutting the proximal end 86 of the assembly handle 85. The screwdriver handle 59 is then reinstalled on the proximal end of the shank and the handle cap 60 reinstalled. The proximal end of the spring 67 abuts the handle 59. The spring is maintained under compression between the assembly handle 85 and screwdriver handle 59. The threaded proximal end 79 of the holding sheath 77 is then inserted into the distal end opening 87A of the assembly handle 85 and the two components are screwed together until the stop ring 91 on the holding sheath shaft 78 engages the distal end 87 of the assembly handle.

Figure 14:
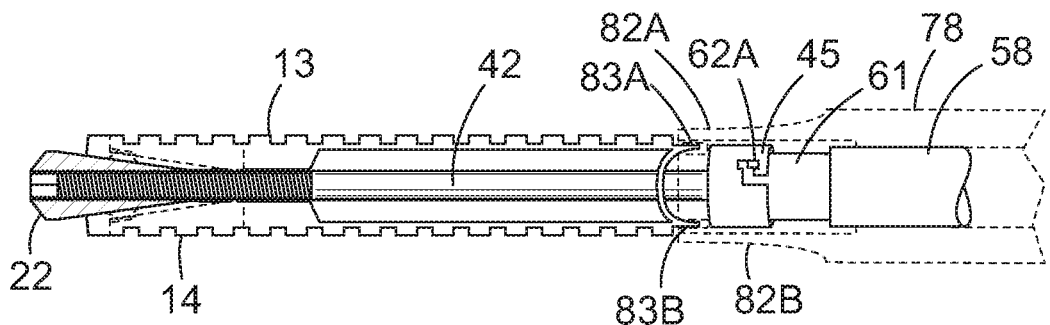
FIG. 14 is a partial side view showing a facet implant held by an implant-screwdriver holding sheath assembly with the diverting nut of the implant and the implant holding sheath illustrated in longitudinal cross-section to reveal the interconnections of the facet implant, facet implant screw, screwdriver, and implant holding sheath in accordance with an example embodiment of a distally expanding facet implant with integrated plate and delivery device.

In order to hold the facet implant 10 with the implant-screwdriver holding sheath assembly 84, the tapered distal end 61 of the screwdriver 55 is inserted inside the crown 45 of the head 43 of the drive screw 41 with the screwdriver guide pins 62A, 62B initially aligned and engaged with vertical entry slot member 49. The screwdriver 55 is then pushed and rotated slightly to move the guide pins 62 through the horizontal connecting slot member 50 and into the vertical function selection slot member 51. The force of the spring 67 functions to push the guide pins toward the proximal end 52 of the vertical function selection slot member 51, which corresponds to the screw pulling position of the screwdriver as best illustrated in FIGS. 13-14. In this position, the simultaneous application of spring force proximally on the head 43 of the drive screw 41 and distally on the mounting arms 82A, 82B urges the proximal edges of the plates 13, 14 of the facet implant 10 into the slots 83A, 83B of the mounting arms and provides stable and secure holding of the facet implant 10 by the implant-screwdriver holding sheath assembly 84. Reversing the insertion process allows the screwdriver 55 to be removed from engagement with the crown 45 of the drive screw.

While the screwdriver 55 is engaged with the crown 45 of the drive screw 41, the drive head 63 of the screwdriver can be brought into screwing position with the drive slot 54 of the screw head 43 in order to rotate the screw. As best seen in FIG. 12B, the screwdriver handle 59 is pushed against the spring force while holding the assembly handle 85. This motion disengages the locking pins 66 on the shank 58 of the screwdriver 55 from the locking teeth 95 on the assembly handle locking ring 92 and pushes the guide pins 62A, 62B toward the distal end of the vertical function selection slot member 51, which corresponds to the screw rotating position of the screwdriver. In this position, the screwdriver can be rotated to rotate the drive screw. When the assembly handle 85 is released, the spring force returns the screwdriver 55 to the initial position in which it is disengaged from the drive screw with the locking pins 66 engaged with the locking teeth 95 of the annular locking ring 92.

2. Structure of Adjacent Cervical Vertebrae

FIG. 18 illustrates the structure of two adjacent cervical vertebrae. Each of the upper vertebra 96 and lower vertebra 97 comprises a large disc-like bony mass anteriorly named the vertebral body, which are separated by a cartilaginous intervertebral disc 98. The distance between the adjacent vertebrae that is essentially filled by the intervertebral disc 98 is referred to as the intervertebral space 99. Posteriorly, each vertebra has an oblique smaller bony mass forming a facet. The upper superior facet 100 and the lower inferior facet 101 of adjacent vertebrae articulate relative to each other at a facet joint 102. The facet joint 102 consists of cartilaginous cushion bounded by a fibrous elastic capsule 103. The external surfaces 104, 105 of the adjacent upper and lower facets 100, 101 respectively are substantially planar and parallel with the longitudinal axis of the cervical spine. A facet joint entrance 106 essentially interrupts the plane of the adjacent external surfaces 104, 105.

Aging and injury can advance the progress of degenerative processes causing the intervertebral disc 98 to loss its elasticity and height leading to a narrowing of the intervertebral space 99 and consequently forward curving of the whole cervical spine or what is called cervical kyphosis. Degenerative changes also can cause narrowing of the facet joint 102. This can result in the intervertebral foramina 108 also narrowing and pressing on the nerves (not shown) as they emerge from the spinal cord (not shown) with resulting cervical radiculopathy and attendant symptoms.

Restoration of the facet joint 102 spacing by simply placing an implant in the joint can improve the intervertebral foramina 108 spacing, however it is likely also to cause narrowing of the intervertebral space 99 and result in various degrees of cervical kyphosis. Alternately, a distally expanding facet implant 10 inserted in the facet joint as described herein is likely to cause a relatively wider expansion of the intervertebral space 99 anteriorly while keeping a narrower inter-facet space posteriorly thus effectively addressing the cause of the radiculopathy without inducing kyphosis. Aided by an integrated inter-facet plate 68 to assist in locking the adjacent facets together posteriorly, the distally expanding facet implant 10 described herein thus provides an effective treatment mechanism.

3. Chisel

Referring to FIGS. 19A-19C, in an example embodiment, a chisel 109 having a particular configuration is adapted to be used to prepare a facet joint, such as facet joint 102, to receive the facet implant 10. In a preferred embodiment, the chisel 109 comprises an elongated rod-like shaft 110 having a proximal end 111 and a distal end 112. Preferably, the transverse cross-sectional shape of the shaft 110 is substantially round, but it also can be of various other shapes. Attached to and extending distally from the distal end 112 is a substantially planar chisel head 113 having a tip 114 and beveled edges 115. The beveled edges can be rounded, right-angled or of various other shapes.

The attachment point between the head 113 and shaft 110 forms a relatively raised shoulder or stopping edge 116. Preferably at least a portion of the stopping edge 116 has an outside dimension that is greater than the dimension of the chisel head 113 transverse to its longitudinal axis, as shown in FIG. 19C, to prevent the shaft 110 from being inserted inside the relatively narrower facet joint 102 when the chisel head 113 is inserted. The distance between the stopping edge 116 and the tip 114 of the chisel head 113 corresponds to the facet depth, i.e., the depth the chisel head 113 is desired to be inserted into the facet joint 102 to prepare the joint to receive the facet implant 10.

A hollow guide pin track 117 runs longitudinally within the shaft 110 from its proximal end 111 and exits the shaft at its distal end 112. At the distal end, the track 117 continues into a guide pin groove 118 formed in the surface of the head 113. This configuration permits the chisel 109 to be introduced within a patient and guided over a pre-inserted guide pin to the precise space of the facet joint 102 in order to cut out the capsule 103 and other tissues in preparation for insertion of the facet implant 10 in the facet joint 102.

4. Rasp

Referring to FIGS. 20A-20C, in an example embodiment, a rasp 119 having a particular configuration is adapted to be used to prepare a facet joint, such as facet joint 102, to receive the facet implant 10. In a preferred embodiment, the rasp 119 comprises an elongated relatively flexible shaft 120 having a proximal end 121 and a distal end 122. A handle 123 is attached at the proximal end 121 of the shaft 120. In one embodiment, the handle 123 preferably comprises a larger preferably cuboidal member to the shaft 120 that passes through it and has a substantially L-shaped cross-section to facilitate gripping the rasp. In an alternative embodiment the handle 123 can be omitted if desired or not needed.

A rasp head 124 is affixed at and extends distally from the distal end 122 of the shaft. The rasp head comprises two substantially planar opposed surfaces 125, 126. The surfaces 125, 126 are substantially roughened. In one embodiment, best shown in FIG. 20C, the rasp head 124 has a relatively thick dimension perpendicular to its longitudinal axis and tapered edges. However, it is understood that the head can take various shapes to achieve the same function. The head 124 tapers to a distal tip 127.

At the distal end 122 of the shaft 120, the transition point from the shaft to the rasp head 124 forms a shoulder or stop ridge 128. The stop ridge 128 preferably has a larger outside dimension than the dimension of the rasp head 124 transverse to its longitudinal axis, as shown in FIG. 20C, to prevent the shaft 120 of the rasp from being introduced into the facet joint 102 when the rasp head 124 is inserted. The distance between the stop ridge 128 and the distal tip 127 of the rasp head 124 corresponds to the desired depth the rasp head 124 is to be inserted inside the facet joint 102.

A hollow guide pin track 129 traverses the shaft 120 longitudinally from the proximal end 121 to the distal end 122 and the rasp head 124 from the point where the head attaches to the distal end of the shaft to the distal tip 127 of the head. This configuration permits the rasp 119 to be introduced within a patient and guided over a pre-inserted guide pin or a guidewire to the facet joint 102 where the rasp head 124 can be inserted into the joint 102 to clean up and roughen the bony facet surfaces in preparation for insertion of the facet implant 10.

5. Guide Plate and Dilator

Referring to FIGS. 21A-21D and 22A-22D, in an example embodiment, a guide plate 130 having a particular configuration is adapted to be used to deliver a dilator 131, also having a particular configuration, to a facet joint, such as facet joint 102, in preparation for delivering the facet implant 10 to the joint for insertion. In a preferred embodiment, the guide plate 130 comprises an elongated substantially planar shaft 132 having a proximal end 133, a distal end 134, and a substantially rectangular cross-section transverse to the longitudinal axis of the shaft. The guide plate 130 is preferably made of a solid relatively rigid material such as various plastic polymers or metals.

The guide plate also comprises a head 135 which is attached at or formed integrally with the distal end 134 of the shaft 132. Preferably, the head 135 is substantially the same shape as the shaft 132 and has the same or smaller transverse cross-sectional size as the shaft. Also preferably, the head 135 has a blunt tapered tip 136 to facilitate insertion into the facet joint 102. In an alternative embodiment the tip 136 can be non-tapered or flat. A hollow guide pin track 137 passes longitudinally through the shaft 132 from the proximal end 133 and exits at the tip 136.

The guide plate further comprises a facet stop mechanism 138 which is preferably located near the distal end 134 of the shaft 132. The facet stop mechanism 138 includes a facet stop lever 139. The facet stop lever 139 can take the form of a substantially cylindrical elongated rod or pin but also can have various other cross-sectional shapes consistent with achieving the functions described for it herein, such as square, elliptical, etc. The facet stop lever 139 resides within an elongated slot or window 140 that extends parallel to the longitudinal axis of the shaft 132 and transversely through the shaft. The stop lever 139 is pivotally connected to the shaft 132 by a pivot pin 141. The pivot pin 141 is mounted to the shaft via solid protrusions or humps 142 formed on the exterior surface of the shaft 132 on opposite longitudinal sides of the slot 140. The pivot pin 141 allows the stop lever 139 to pivot on the pivot pin parallel to and in alignment with the longitudinal axis of the shaft 132 in the elongated slot 140.

Extending through the stop lever 139 transversely and at an oblique angle with respect to its longitudinal axis is a guide pin passage 143. The position of the guide pin passage and its angle in relation to the stop lever 139 are such that when the stop lever is pivoted into a tilted position at an acute angle with respect to the longitudinal axis of the shaft 132, such as shown in FIG. 21C, the guide pin passage 143 aligns with the guide pin track 137 passing longitudinally through the shaft 132. In this configuration, when the guide plate 130 is passed over a guide pin, as described below, the guide pin passes through the guide pin track 137 and aligned guide pin passage 143 and locks the stop lever 139 in the tilted position. Preferably, the angle between the tilted stop lever 139 and the longitudinal axis of the shaft 132 that results in alignment of the guide pin passage 143 and the guide pin track 137 is relatively small to facilitate delivery of the guide plate to the facet joint 102 but is large enough so that the ends of the stop lever 139 protrude sufficiently from the shaft 132 to engage the exterior facet surfaces 104, 105 of the of the vertebrae 96, 97 adjacent the facet joint 102 when the head 135 of the guide plate enters the joint. Depending on the relative dimensions of the shaft 132 and stop lever 139, an acute angle in the range of approximately 40-60 degrees typically will be sufficient to achieve the desired objectives.

When the guide plate 130 has reached the desired position with the stop lever 139 in contact with the exterior facet surfaces 104, 105 and the head 135 of the guide plate inside the facet joint, the guide pin can be removed. Removing the guide pin releases the facet stop lever 139 from the locked tilted position. Further insertion of the head 135 into the facet joint then causes the stop lever to pivot into a substantially perpendicular position relative to the shaft 132 and in contact with the external facet surfaces 104, 105 at the facet joint entrance 106, thus blocking further advancement of the guide plate 130 inside the facet joint 102 to prevent over-insertion. The position of the facet stop lever 139 on the shaft 132 relative to the head 135 thus controls the extent to which the guide plate 130 is permitted to extend inside the facet joint 102.

Referring to FIGS. 22A-22D, the dilator 131 comprises an elongated shaft 144 having a proximal end 145, a distal end 146, an upper surface 147, and a lower surface 148. As seen in FIG. 22B, the transverse cross-sectional shape of the shaft 144 can vary from substantially square to substantially rectangular, and the cross-sectional dimensions can also vary, depending on the degree of dilation desired, as described in further detail below. Other cross-sectional shapes also may be employed consistent with the ability to provide adequate dilation. A hollow guide plate track 149 extends within the shaft 144 between the proximal and distal 146 ends substantially coaxially with the longitudinal axis of the shaft 144. As seen in FIGS. 22B and 22C, and as described below, the guide plate track 149 is shaped and dimensioned to cooperate with the guide plate 130.

In a preferred embodiment, the distal end 146 of the shaft 144 terminates in a narrowed head 150. However, in an alternative embodiment the head can be substantially the same size as the shaft 144. The head 150 terminates distally in a facet contact surface 151 which in a preferred embodiment is oriented at an oblique angle of less than 90 degrees with respect to the upper surface 147 of the shaft 144. The obliquely-angled facet contact surface 151 helps in achieving better contact with the obliquely-oriented facet joint outer surfaces 104, 105. However, in an alternative embodiment the facet contact surface 151 can be substantially perpendicular to the upper surface 147 if desired.

In one embodiment, the facet contact surface 151 can have an elongated substantially vertical facet stop slot 152 that extends the height of the facet contact surface 151 between the upper 147 and lower 148 surfaces of the shaft 144. The facet stop slot 152 is configured and adapted to fit and engage the facet stop lever 139 of the guide plate 130.

Dilatation is carried out prior to insertion of the facet implant 10 in order to create an adequate passage for delivery of the facet implant 10 to the facet joint 102. Dilation is carried out by serially passing dilators 131 of various cross-sectional sizes sequentially from smaller to larger over the guide plate 130 while the head 135 of the guide plate is inserted in the facet joint 102.

6. Introducer Sheath

Referring to FIG. 23, in an example embodiment, an introducer sheath 153 having a particular configuration is adapted to be used to deliver the facet implant 10 to the affected facet joint 102 for insertion. The introducer sheath 153 comprises a rigid hollow elongated structure having a proximal end 154, a distal end 155, an upper surface 156, and a lower surface 157. The interior of the introducer sheath defines a substantially cuboidal hollow shaft or lumen 158 that extends from the proximal end 154 to the distal end 155. Alternatively, the shaft can assume other cross-sectional shapes that achieve the same function. In a preferred embodiment, the distal end 155 terminates in an obliquely-angled facet contact surface 159, which is angled less than 90 degrees in relation to upper surface 156 and which extends in a generally proximal direction from the upper surface 156 to the lower surface 157. In an alternative embodiment, the facet contact surface 159 can be substantially perpendicular in relation to the longitudinal axis of the shaft 158 if desired. The substantially cuboidal shaft or lumen 158 is shaped and sized to facilitate passage of the introducer sheath 153 over the drill guide 160, described below, such that the introducer sheath 153 can be inserted within a patient over the drill guide 160 until the facet contact surface 159 comes in contact with the facet external surfaces 104, 105.

7. Drill Guide

Figure 24B:
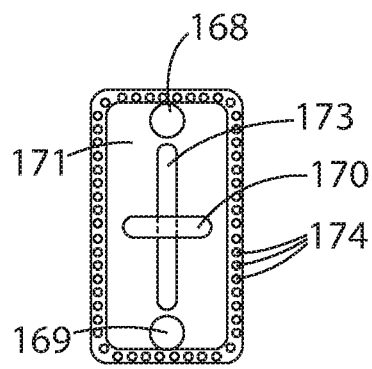
FIG. 24B is a proximal end view of the drill guide of FIG. 24A in accordance with an example embodiment of a distally expanding facet implant with integrated plate and delivery device.

Referring to FIGS. 24A-24B, in an example embodiment, a drill guide 160 having a particular configuration is adapted to be used with the guide plate 130 to facilitate drilling boreholes in the proper positions in the external facet surfaces 104, 105 of adjacent vertebrae 96, 97 in preparation for fastening the inter-facet plate 68 to the adjacent vertebrae to stabilize the facet implant 10 and help fuse the adjacent vertebrae.

The drill guide 160 comprises an elongated preferably cuboidal shaft 161 having a proximal end 162, a distal end 163, an upper surface 164, and a lower surface 165. Alternatively, the shaft can be cylindrical or any other shape consistent with achieving its described functions. The shaft 161 is preferably solid or mostly solid. A substantially annular crown-shaped guard ring 166 having a proximal face 167 is removably attached to and extends proximally from the proximal end 162 of the shaft 161. The guard ring 166 preferably has an outside diameter greater than the outside dimension of the shaft 161 and serves a number of purposes including improving the operator's grip, protecting the operator's hands, facilitating the insertion of drill bits, and stopping the drill bits from drilling beyond a preselected borehole depth, as described below.

Three parallel hollow tracks 168, 169, 170 longitudinally traverse the shaft between the proximal 162 and distal 163 ends terminating in three openings in the distal end. The tracks also extend through the guard ring 166 terminating in three openings (not shown) in the proximal face 167. Preferably the openings in the proximal face 167 are substantially tapered or funnel-shaped to facilitate insertion of drill bits in the tracks as described below. One track 168 comprises an upper drill bit track and is located in proximity to the upper surface 164. The second track 169 comprises a lower drill bit track and is located in proximity to the lower surface 165. The third track 170 comprises a guide plate track and is located at or close to the central longitudinal axis of the shaft 161 between the upper and lower drill bit tracks 168, 169. The distances between the respective drill bit tracks 168, 169 and the guide plate track 170 correspond to the desired distances between the facet joint entrance 106 and the respective facet boreholes to be drilled in the facet external surfaces 104, 105 of the adjacent vertebrae 96, 97.

The distal end 163 of the shaft 161 preferably terminates in an obliquely-angled facet contact surface 171 which is angled less than 90 degrees in relation to the upper surface 164 and which extends in a generally proximal direction from the upper surface 164 toward the lower surface 165. The facet contact surface 171 includes an inwardly curved portion or a form of indentation comprising a facet joint curve 172, which is adapted to improve the fit of the facet contact surface 171 over the facet external surfaces 104, 105 and facet joint entrance 106. In one embodiment, the facet contact surface 171 includes a vertical groove substantially perpendicular to the longitudinal axis of the guide plate track comprising a facet stop lever slot 173. The facet stop lever slot 173 is adapted to engage the facet stop lever 139 of the guide plate 130 to prevent the lever from stopping short of contacting the facet surface and to stabilize and minimize rotational movement of the drill guide. A plurality of spikes 174 are distributed around the periphery of the facet contact surface 171 and are adapted to engage the external facet surfaces 104, 105 to stabilize the drill guide 160 and minimize any movement during drilling.

F. Method of Use and Operation of Preferred Embodiment

Figure 25:
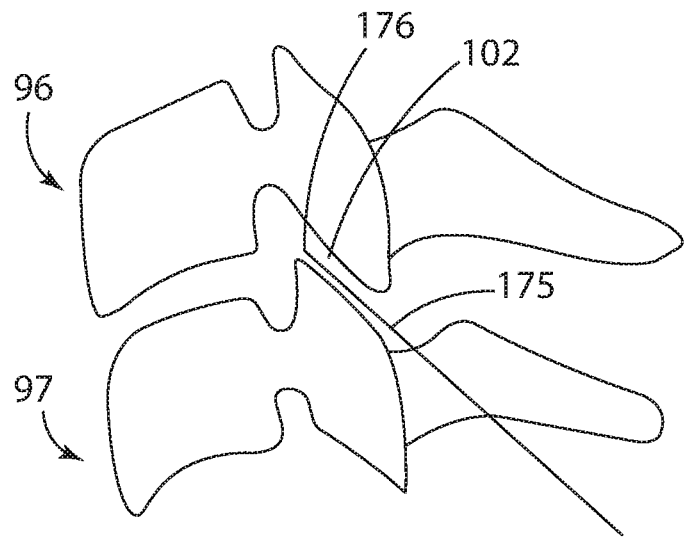
FIG. 25 is a lateral view of a guide pin being inserted into a facet joint between adjacent cervical vertebrae in accordance with an example embodiment of a distally expanding facet implant with integrated plate and delivery device.

Referring primarily to FIGS. 25-37, use and operation of an example embodiment will now be described. FIG. 25 illustrates an initial step in the process of inserting the facet implant 10 into an affected facet joint 102. Initially, an elongated guide pin 175 having a distal tip 176 is inserted into the facet joint 102 posteriorly either percutaneously under X-ray guidance, under direct vision, under endoscopic guidance, or through a previously inserted hollow needle. The guide pin 175 is preferably relatively stiff to facilitate insertion and delivery of the facet implant 10 and the various joint preparation and implant delivery components described herein through the tissue of a patient to the facet joint 102. However, the distal tip 176 is preferably relatively blunt and less stiff to minimize trauma to the important structures surrounding the facet joint. As used herein, the term "guide pin" is not necessarily intended to be limited to a pin but may also include a wire having sufficient stiffness and strength to achieve the described objectives.

Figure 26:
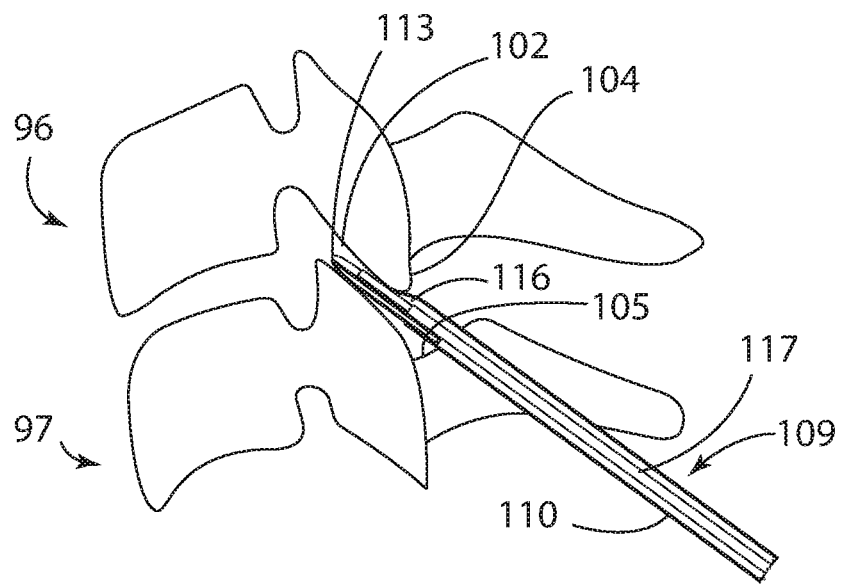
FIG. 26 is a lateral view showing a chisel illustrated partially in longitudinal cross-section being inserted into the facet joint as shown in FIG. 25 in accordance with an example embodiment of a distally expanding facet implant with integrated plate and delivery device.

In another step, illustrated in FIG. 26, the chisel 109 is inserted and guided over the guide pin 175, i.e., with the guide pin track 117 in the elongated shaft 110 of the chisel passing over the guide pin 175, until the chisel head 113 enters the facet joint 102 and the raised stopping edge 116 abuts the external surfaces 104, 105 of the adjacent vertebrae 96, 97 adjacent the facet joint entrance 106. The guide pin 175 is removed through the guide pin track 117 and the chisel is manipulated to cut the capsule and other tissues within the facet joint as necessary or desired in preparation for subsequent insertion of the facet implant 10. The guide pin 175 is then reinserted through the guide pin track 117 and the chisel 109 is removed over the guide pin.

In another step (not separately illustrated but substantially the same as FIG. 26), if desired or necessary, the rasp 119 may be inserted and guided over the guide pin 175, i.e., with the guide pin track 129 in the elongated shaft 120 of the rasp passing over the guide pin 175, until the rasp head 124 enters the facet joint 102 and the stop ridge 128 abuts the external facet surfaces 104, 105 of the adjacent vertebrae 96, 97 adjacent the facet joint entrance 106. The guide pin 175 is then removed through the guide pin track 129 and the rasp is manipulated to roughen the boney surfaces within the facet joint as necessary or desired in preparation for subsequent insertion of the facet implant 10. The guide pin 175 is then reinserted through the guide pin track 129 and the rasp 119 is removed over the guide pin.

Figure 27:
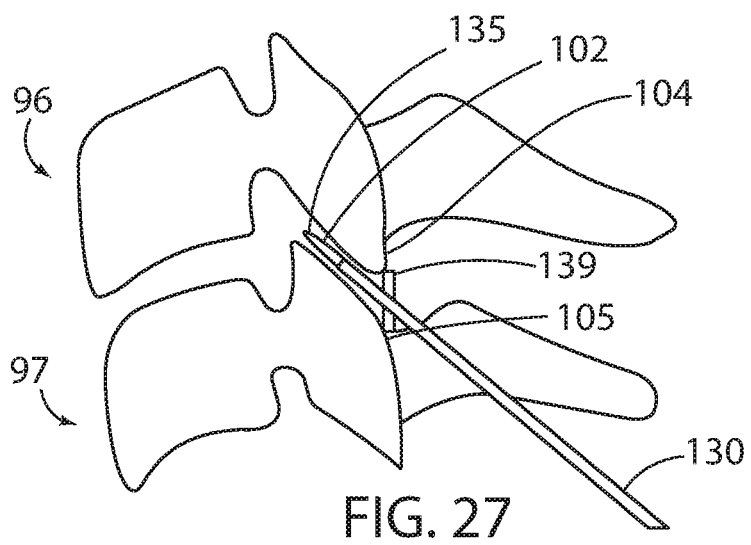
FIG. 27 is a lateral view showing a facet guide plate being inserted into the facet joint as shown in FIG. 26 in accordance with an example embodiment of a distally expanding facet implant with integrated plate and delivery device.

After the facet joint 102 has been prepared using the chisel 109 and rasp 119, in another step, illustrated in FIG. 27, the guide plate 130 is inserted and guided over the guide pin 175, i.e., with the guide pin track 137 in the elongated shaft 132 of the guide plate and the aligned guide pin passage 143 of the facet stop lever 139 passing over the guide pin 175, until the head 135 of the guide plate slides inside the joint 102 and the facet stop lever 139 abuts the external facet surfaces 104, 105. The guide pin is then removed, unlocking the facet stop lever from the tilted position. The head is then further inserted into the facet joint until the facet stop lever assumes a substantially perpendicular position in contact with the external facet surfaces 104, 105, of the adjacent vertebrae preventing the guide plate from sliding further into the joint. Alternatively, the guide plate 130 can be inserted visually under manual control without the aid of guide pin 175.

Figure 28:
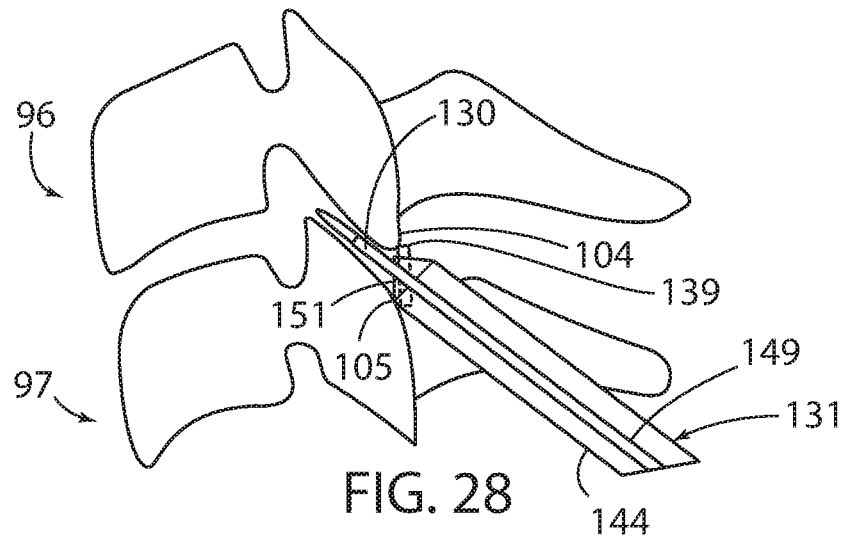
FIG. 28 is a lateral view showing a dilator illustrated partially in longitudinal cross-section being inserted over the guide plate into the facet joint as shown in FIG. 27 in accordance with an example embodiment of a distally expanding facet implant with integrated plate and delivery device.

In another step, illustrated in FIG. 28, the dilator 131 is inserted over the guide plate 130, i.e., with the guide plate track 149 in the elongated shaft 144 of the dilator 131 passing over the guide plate 130 until the facet contact surface 151 of the dilator 131 abuts the external facet surfaces 104, 105 and the facet stop slot 152 of the dilator 131 abuts and engages the facet stop lever 139 of the guide plate 130. The dilator 131 is employed to dilate the passage from the skin level to the facet joint external surfaces 104, 105 to facilitate delivery of the facet implant 10 to the facet joint 102. Dilators of successively larger sizes can be sequentially inserted and guided to the facet joint 102 over the guide plate 130 until the necessary or desired dilatation is reached. Once a sufficient degree of dilation is achieved, the dilator 131 is removed over the guide plate 130.

Figure 29:
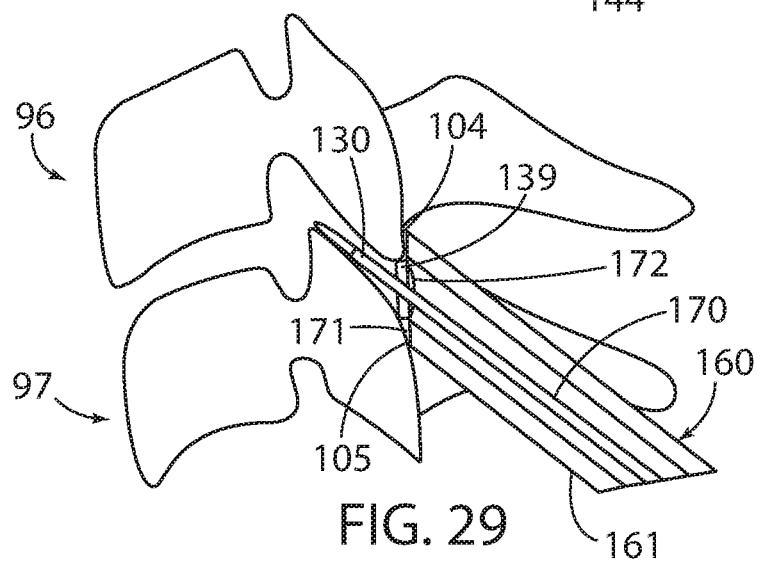
FIG. 29 is a lateral view showing a drilling guide illustrated partially in longitudinal cross-section being inserted over the guide plate up to the facet joint as shown in FIG. 28 in accordance with an example embodiment of a distally expanding facet implant with integrated plate and delivery device.
Figure 30:
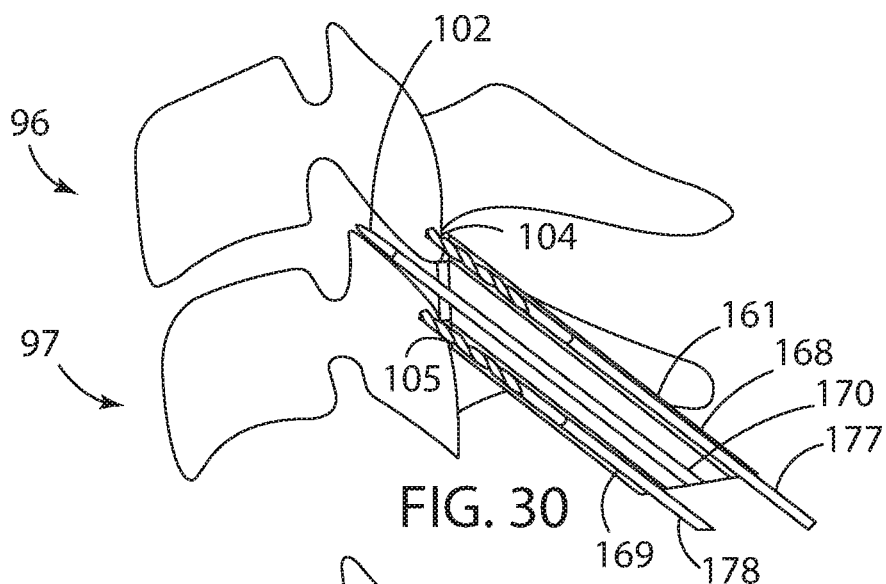
FIG. 30 is a lateral view showing drill bits being inserted through a drill guide illustrated partially in longitudinal cross-section and drilling boreholes in the superior and inferior facets of the facet joint as shown in FIG. 29 in accordance with an example embodiment of a distally expanding facet implant with integrated plate and delivery device.
Figure 31:
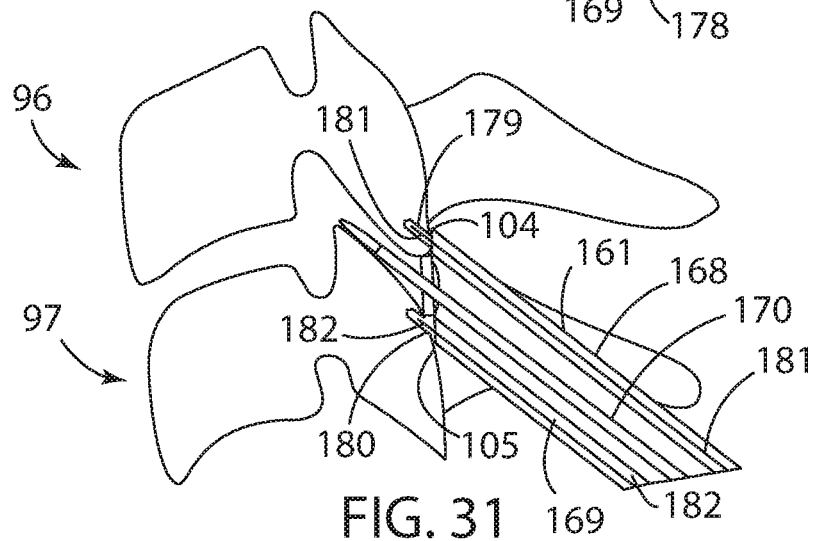
FIG. 31 is a lateral view showing borehole guidewires being inserted through the drill guide illustrated partially in longitudinal cross-section into the boreholes in the superior and inferior facets of the facet joint as shown in FIG. 30 in accordance with an example embodiment of a distally expanding facet implant with integrated plate and delivery device.

In other steps, illustrated in FIGS. 29-31, the drill guide 160 is inserted over the guide plate 130, i.e., with the guide plate track 170 in the elongated shaft 161 of the drill guide 160 passing over the guide plate 130, until the facet contact surface 171 and facet joint curve 172 of the drill guide 160 abut the external facet surfaces 104, 105 and the facet stop lever slot 173 of the drill guide 160 abuts and engages the facet stop lever 139 of the guide plate 130. Suitable drill bits 177, 178 having elongated shanks are then inserted in the openings (not shown) in the proximal face 167 of the guard ring 166 of the drill guide 160 and guided though the upper and lower drill bit tracks 168, 169 respectively into contact with the respective upper and lower external facet surfaces 104, 105 of the upper and lower vertebrae 96, 97 adjacent the affected facet joint 102. The drill bits are then operated to drill upper and lower facet boreholes 179, 180 in the respective upper and lower external facet surfaces 104, 105. The spikes 174 distributed around the periphery of the facet contact surface 171 of the drill guide 160, in conjunction with the guide plate 130 and facet stop lever 139 engaged in the facet stop lever slot 173, assist in holding the drill guide in place relative to the external facet surfaces 104, 105 during the drilling process so that the boreholes 179, 180 can be accurately and precisely created. Once the boreholes are created, the drill bits are removed through the upper and lower drill bit tracks 168, 169 and upper and lower borehole guidewires 181, 182 are inserted in the drill bit tracks and guided into the upper and lower boreholes 179, 180 respectively.

Figure 32:
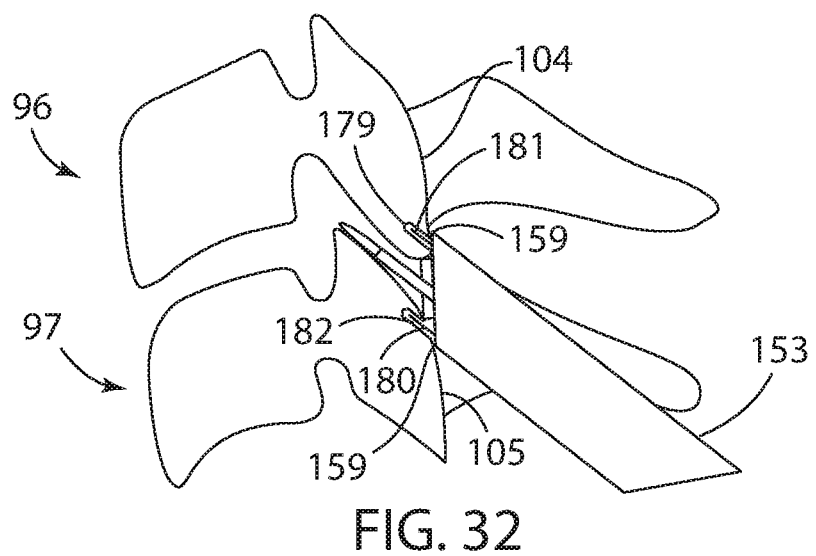
FIG. 32 is a lateral view showing an introducer sheath being inserted over the drill guide up to the facet joint as shown in FIG. 31 in accordance with an example embodiment of a distally expanding facet implant with integrated plate and delivery device.
Figure 33:
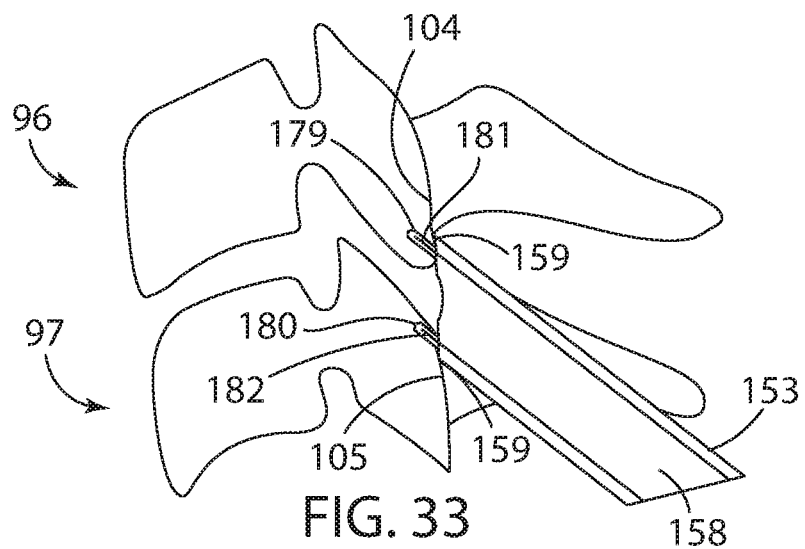
FIG. 33 is a lateral view with the introducer sheath illustrated partially in longitudinal cross-section showing the borehole guidewires remaining inside the drilled boreholes in the superior and inferior facets of the facet joint as shown in FIGS. 31-32 after removal of the drill guide in accordance with an example embodiment of a distally expanding facet implant with integrated plate and delivery device.

In other steps, illustrated in FIGS. 32-33, the guard ring 166 is removed from the shaft 161 of the drill guide 160, and the introducer sheath 153 is then inserted and guided over the drill guide 160, i.e., with the elongated internal shaft 158 of the introducer sheath 153 passing over the elongated shaft 161 of the drill guide 160, until the facet contact surface 159 of the introducer sheath 153 abuts the external facet surfaces 104, 105 of the vertebrae 96, 97 adjacent the facet joint entrance 106. The drill guide 160 and guide plate 130 are then retracted through the internal shaft 158 of the introducer sheath 153 leaving the introducer sheath and borehole guidewires 181, 182 in place.

Figure 34:
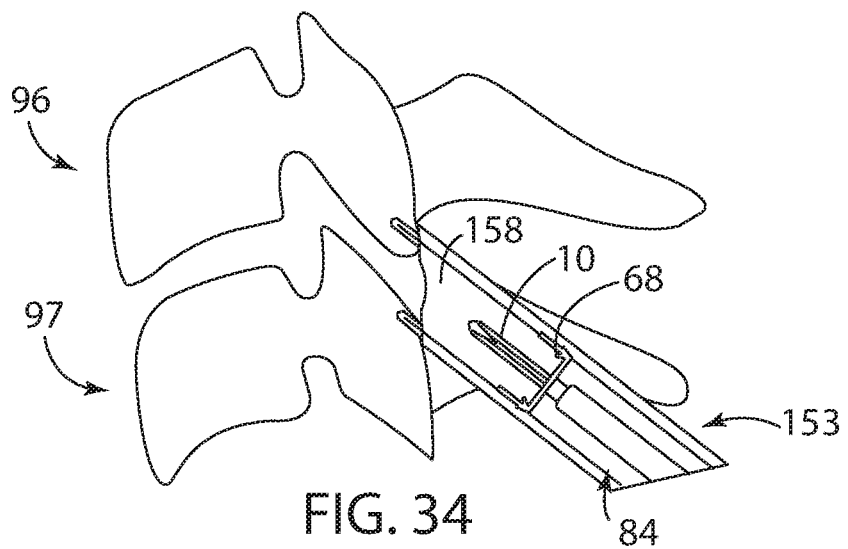
FIG. 34 is a lateral view with the introducer sheath illustrated partially in longitudinal cross-section showing a facet implant held by an implant-screwdriver mounting sheath assembly being slid over the borehole guidewires through the introducer sheath as shown in FIG. 33 toward the facet joint in accordance with an example embodiment with the facet implant of a distally expanding facet implant with integrated plate and delivery device.
Figure 35:
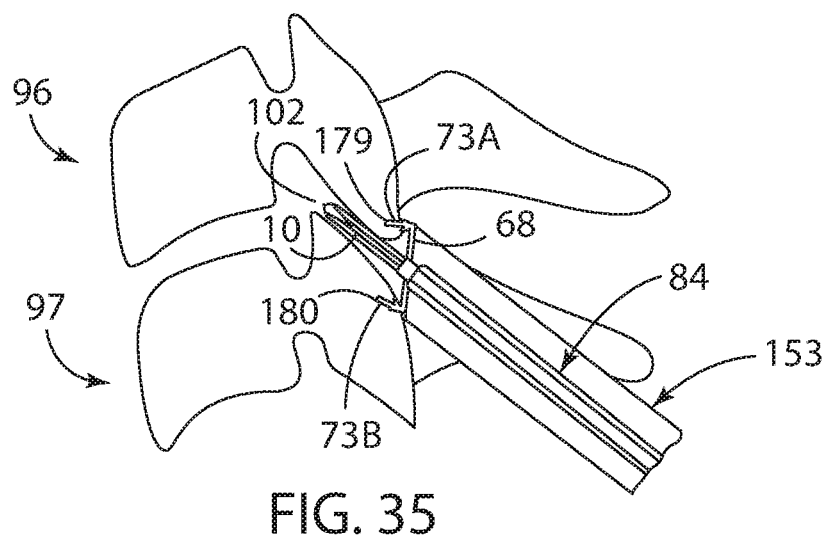
FIG. 35 is a lateral view with the introducer sheath illustrated partially in longitudinal cross-section showing the facet implant as shown in FIG. 34 being introduced into the facet joint and facet plate pins being inserted within the drilled facet boreholes in accordance with an example embodiment of a distally expanding facet implant with integrated plate and delivery device.

In other steps, illustrated in FIGS. 34-35, the facet implant 10 and integrated inter-facet plate 68, which are mounted on and held by the implant-screwdriver holding sheath assembly 84 as described above, are introduced and guided through the internal shaft 158 of the introducer sheath 153 until the facet implant 10 resides inside the facet joint 102 and the facet pins 73A, 73B of the inter-facet plate 68 are seated in the facet boreholes 179, 180. The borehole guidewires 181, 182 are used to help guide the facet pins into the facet boreholes and may then be removed through the internal shaft 158 of the introducer sheath 153.

Figure 36:
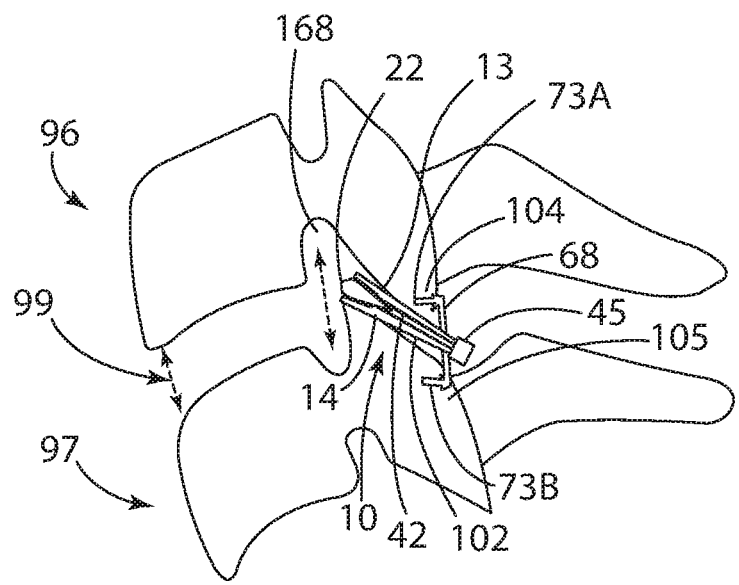
FIG. 36 is a lateral view showing the facet implant of FIG. 35 inside the facet joint with the distal end of the facet implant expanded and the intervertebral space distracted in accordance with an example embodiment of a distally expanding facet implant with integrated plate and delivery device.
Figure 37:
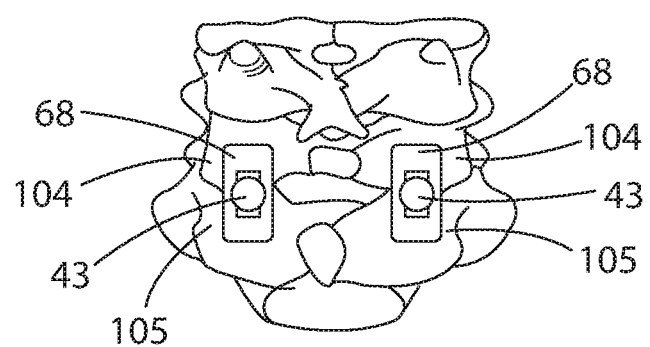
FIG. 37 is a posterior view showing two adjacent cervical vertebrae with facet implants and intervertebral bridges installed in both lateral facet joints.

In other steps, illustrated in FIGS. 36-37, once the facet implant 10 is deployed inside the facet joint 102, the screwdriver 55 is manipulated to help position the facet implant in the joint and to divert the distal ends 12 of the implant plates 13, 14. Initially, the screwdriver is in the screw pulling position in the implant-screwdriver holding sheath assembly 84 as described previously. In this position, the screwdriver can be used, if desired or necessary, to pull the screw 41 in a posterior direction while the holding sheath 77 is pushing on the proximal end 11 of the upper and lower plates 13, 14 of the facet implant 10 further stabilizing the implant grip. This can help position the implant in the joint and begin moving the coupled diverting nut 22 further between the plates 13, 14 to begin diverting the distal ends 12 of the plates. As the distal ends divert, the implant expands in the joint and begins to engage the bony facet surfaces of the joint.

The screwdriver may then be repositioned into the screw rotating position within the implant-screwdriver holding sheath assembly 84 as previously described. The screwdriver 55 is then rotated to rotate the head 43 of the drive screw 41 to further tighten the drive screw relative to the diverting member 20 of the facet implant. This causes the moveable diverting nut 22 of the diverting member to further move proximally in sliding engagement with the stationary diverting mass 21 of the diverting member, which is attached to the inner surfaces 17 of the implant plates 13, 14. The further movement of the diverting nut in engagement with the diverting mass causes the distal ends 12 of the plates 13, 14 to further divert away from each other as described above without substantially diverting the proximal ends of the plates. At the same time, tightening the drive screw 41 relative to the diverting member 20 causes the facet pins 73 of the inter-facet plate 68 to securely embed within the facet boreholes 179, 180 and the anchoring teeth 74 to securely engage with the external facet surfaces 104, 105.

Once the drive screw 41 has been tightened to provide the necessary or desired amount of distraction of the facet joint 102, the screwdriver is disengaged from the drive screw and the implant-screwdriver holding sheath assembly 84 and introducer sheath 153 are removed leaving the expanded facet implant 10 in place. FIG. 37 provides a posterior view of the facet implant 10 with integrated inter-facet plate 68 inserted in and at the facet joint 102 on both lateral sides of adjacent upper and lower vertebrae 96, 97 of the cervical spine. If desired or necessary, additional steps can be performed before removing the introducer sheath 153 including, for example, injecting bone paste inside and around the facet implant to facilitate joint fusion in the future.

A beneficial effect of the insertion and expansion of the facet implant 10 as described is that the facet joint 102 is distracted distally, which results in widening of both the intervertebral disc space 99 and intervertebral foramina 108 and provides relief from the symptoms of cervical radiculopathy. Another beneficial effect is that distraction of the facet joint 10 distally maintains or restores the natural lordosis of the cervical spine while avoiding the condition of kyphosis. This effect is enhanced by the inclusion of the integral inter-facet plate 68, which helps lock the adjacent vertebrae 96, 97 together and stabilizes them in a natural lordotic position, further preventing the facet joint 102 from diverting proximally, and further guarding against inducing a condition of kyphosis.

Unless otherwise defined, all technical and scientific terms used herein have the same meaning as commonly understood by one of ordinary skill in the art to which this invention belongs. Although methods and materials similar to or equivalent to those described herein can be used in the practice or testing of the distally expanding facet implant with integrated plate and delivery device, suitable methods and materials are described above. All publications, patent applications, patents, and other references mentioned herein are incorporated by reference in their entirety to the extent allowed by applicable law and regulations. The distally expanding facet implant with integrated plate and delivery device may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

What is claimed is:

1. An implant for a cervical intervertebral facet joint, comprising:
    first and second plates spaced apart in opposition and each having a first end and a second end;
    a diverting member positioned between the first and second plates and moveable in engagement with the first and second plates in a direction between the first end and the second end of the first and second plates; and
    a driving member coupled with the diverting member, wherein the driving member is operable to cause the diverting member to move in the direction between the first end and the second end of the first and second plates to cause the plates to divert away from each other at and near their respective first ends without diverting away from each other at their respective second ends;
    wherein the implant is adapted for insertion in a facet joint, wherein the implant has a first state in which the first ends of the respective first and second plates are not diverted away from each other and a second state in which the first ends of the respective first and second plates are diverted away from each other, wherein the implant is adapted in the first state to be inserted in a facet joint, and wherein the implant is operable in the second state to cause anterior distraction of a facet joint without inducing kyphosis; wherein the respective second ends of the first and second plates are connected by a connector that is adapted to allow the respective second ends of the first and second plates to compress relative to each other and to prevent the respective second ends of the first and second plates from diverting away from each other.

2. The implant of claim 1 wherein the diverting member is interposed between the first ends of the respective first and second plates and comprises an elongated diverting nut having a first member and a second member, wherein the first member and the second member are longitudinally spaced, wherein the first member has an angled tip adapted for insertion in a facet joint, wherein the second member comprises a top surface and a bottom surface, and wherein when the implant is in the second state substantially the entire top surface is in engagement with the first plate and substantially the entire bottom surface is in engagement with the second plate.

3. The implant of claim 2 wherein at least one of the first and second plates includes a track comprising an elongated slot between the first end and second end, wherein the diverting member includes a fin that projects into and is retained in the slot, and wherein the fin is in sliding engagement with the slot so that the diverting member is limited to be moved in the direction between the first end and the second end of the first and second plates while remaining in engagement with the at least one of the first and second plates.

4. The implant of claim 3, wherein the fin is substantially t-shaped with a cross-member portion, and wherein the cross-member portion is retained by the slot.

5. The implant of claim 1, wherein the diverting member comprises a stationary component connected to the first and second plates, and a moveable component adapted for moveable engagement with the stationary component.

6. The implant of claim 5, wherein the driving member is coupled with the moveable component of the diverting member.

7. The implant of claim 6, wherein:
    the stationary component of the diverting member comprises a first engagement surface that extends substantially a width of the first and second plates and that has a first shape;
    the moveable component of the diverting member comprises a second engagement surface that extends substantially a width of the diverting member and that has a second shape complementary to the first shape; and
    the second engagement surface is adapted for moveable engagement with the first engagement surface.

8. The implant of claim 7, wherein the first shape comprises a first angled slope and the second shape comprises a second angled slope complementary to the first angled slope.

9. The implant of claim 8, wherein the second engagement surface is adapted for sliding engagement with the first engagement surface.

10. The implant of claim 9, wherein the first and second angled slopes are relatively oriented so that only motion of the moveable component in a direction away from the first ends of the respective first and second plates causes the first ends to divert away from each other.

11. The implant of claim 7, wherein the diverting member comprises a lock adapted to prevent moveable engagement of the second engagement surface with the first engagement surface in a direction toward the first ends of the plates.

12. The implant of claim 11, wherein the lock comprises a first set of protrusions of a selected shape on one of the first and second engagement surfaces and a first set of correspondingly shaped recesses on the other of the first and second engagement surfaces.

13. The implant of claim 5 wherein:
    the driving member comprises an elongated screw adapted for rotation; and
    the screw has a first end rotatably coupled with the moveable component of the diverting member and a second end comprising a head adapted for engagement to impart rotational motion to the screw relative to the diverting member;
    whereby rotation of the screw relative to the diverting member causes the moveable component of the diverting member to move in engagement with the stationary component of the diverting member.

14. The implant of claim 13 wherein the head of the screw comprises a function selection slot with positions corresponding to rotation and pulling of the screw.

15. The implant of claim 14 including a screwdriver comprising:
    a pin adapted to engage the function selection slot and to be selectively moveable within the slot between the positions corresponding to rotation and pulling of the screw; and a drive head adapted to engage the head of the screw to impart rotational movement to the screw when the pin is in the position corresponding to rotation of the screw.

16. The implant of claim 15 including a device adapted to hold the implant for delivery to and insertion in the facet joint, the device comprising:
an elongated sheath having a first end, a second end, and an interior passage; and
a handle having an interior passage;
wherein the first end of the elongated sheath comprises a holding arm adapted to engage and hold the implant;
wherein the second end of the elongated sheath is coupled with the handle with the interior passages of the handle and the elongated sheath in communication; and
wherein the screwdriver is moveably coupled with the handle and extends through the interior passages of the of the handle and elongated sheath such that the screwdriver can be manipulated to selectively engage the head of the screw with the pin and drive head while the implant is held by the holding arm.

17. The implant of claim 16 wherein the second end of the elongated sheath is coupled with the handle via corresponding threads on the second end of the sheath and the handle.

18. The implant of claim 16 wherein the device comprises a spring coupled with the handle and the screwdriver such that when the pin and drive head of the screwdriver are engaged with the head of the screw the spring exerts a force urging the implant into engagement with the holding arm.

19. The implant of claim 18 wherein the force exerted by the spring urges the pin into the screw pulling position in the function selection slot of the head of the screw and wherein the screwdriver is adapted to be manipulated to selectively move the pin into the screw rotation position in the function selection slot against the force exerted by the spring.

20. The implant of claim 16 wherein the holding arm is adapted to engage and hold the first and second plates of the implant.

21. The implant of claim 20 including an inter-facets plate, wherein the inter-facets plate:
is adapted to be fastened to the external posterior facet surfaces of the vertebrae adjacent to the facet joint in which the implant is to be inserted to interconnect the vertebrae;
is coupled between the screw and the first and second plates of the implant;
has an access way for the holding arm to engage and hold at least one of the first and second ends of the first and second plates.

22. The implant of claim 21 wherein the holding arm comprises a protrusion with a slot adapted to engage and hold at least one of the first and second ends of the first and second plates.

23. The implant of claim 1, wherein each of the first and second plates comprises a first surface having a plurality of protrusions, wherein the protrusions are adapted to engage with a surface of a facet joint when the implant is in the second state.

24. The implant of claim 23 wherein the first surface of each of the first and second plates comprises a plurality of recesses interposed with the plurality of protrusions, wherein the recesses are adapted to fuse the implant with a facet joint when the implant is in the second state.

25. The implant of claim 1 including an inter-facet plate, wherein the inter-facet plate is:
engaged with the driving member;
adapted to be fastened to the external posterior facet surfaces of the vertebrae adjacent to a cervical intervertebral facet joint in which the implant is to be inserted; and
operable in response to operation of the driving member causing the plates of the implant to divert away from each other to substantially lock the external posterior facets of the adjacent vertebrae together to prevent posterior distraction of the facet joint.

26. The implant of claim 25 wherein the inter-facet plate is adapted to be oriented with respect to the first and second plates to span the posterior opening of the facet joint in which the implant is to be inserted, and comprises an adjustment slot adapted to allow the position of the implant to be adjusted vertically and angularly relative to the inter-facet plate.

27. The implant of claim 26 wherein the inter-facet plate comprises:
a surface adapted to face the external posterior facet surfaces of a first vertebra and a second vertebra adjacent to the facet joint in which the implant is to be inserted;
a first pin having a base attached to the surface and adapted to be inserted into the external posterior facet surface of the first vertebra adjacent to the facet joint in which the implant is to be inserted; and
a second pin having a base attached to the surface and adapted to be inserted into the external posterior facet surface of the second vertebra adjacent to the facet joint in which the implant is to be inserted.

28. The implant of claim 27 wherein the first pin and the second pin each comprise:
a passage adapted to receive a first guide pin and a second guide pin respectively for guiding the first and second pin respectively to a selected area of the external posterior facet surface of the first and second vertebra respectively.

29. The implant of claim 28 wherein the passage comprises:
an interior passage through the first pin and second pin respectively; and
an exterior groove in communication with the interior passage.

30. The implant of claim 29 wherein the inter-facet plate includes a plurality of teeth adapted to engage the external posterior facet surface of the first vertebra and the second vertebra.

31. The implant of claim 1 including a chisel device for preparing a facet joint to receive the implant, wherein the chisel device comprises:
an elongated shaft having a first end and a second end;
a chisel head attached to the second end;
a guide pin passage extending through the shaft between the first end and the second end and adapted to receive a guide pin for guiding the chisel device;
a guide pin groove in the chisel head in communication with the guide pin passage and adapted to receive the guide pin; and
a stop edge between the chisel head and the second end of the elongated shaft adapted to engage the exterior facets surfaces of vertebrae adjacent to the facet joint and to permit insertion of the chisel head while preventing over-insertion of the shaft.

32. The implant of claim 1 including a rasp device for preparing a facet joint to receive the implant, wherein the rasp device comprises:
an elongated shaft having a first end and a second end;

a rasp head attached to the second end;
a guide pin passage extending through the shaft between the first end and the second end and through the rasp head for guiding the rasp device; and
a stop edge between the rasp head and the second end of the elongated shaft adapted to engage the exterior facets surfaces of vertebrae adjacent to the facet joint and to permit insertion of the rasp head while preventing over-insertion of the shaft.

33. The implant of claim 1 including a guide plate for facilitating the delivery of devices adapted to prepare a facet joint to receive the implant, wherein the guide plate comprises:
a first elongated shaft having a longitudinal axis, a first end and a second end, wherein the first end comprises a head adapted for posterior insertion in a facet joint;
a guide pin passage extending through the first elongated shaft between the first end and the second end and through the head for guiding the guide plate;
an elongated facet stop lever pivotably attached to the first elongated shaft near the first end, wherein the facet stop lever is adapted to pivot into a stop position and to engage exterior facets surfaces of the vertebrae adjacent to a facet joint in which the implant is to be inserted to prevent over-insertion of the shaft.

34. The implant of claim 33 wherein:
the first elongated shaft includes an elongated stop lever slot that intersects the guide pin passage; and
the facet stop lever is adapted to pivot within the stop lever slot and includes a stop lever guide pin passage that aligns with the guide pin passage in the first elongated shaft when the facet stop lever is pivoted at a selected angle relative to the longitudinal axis of the first elongated shaft;
whereby upon insertion of a guide pin through the guide pin passage and the aligned stop lever guide pin passage, the facet stop lever is maintained in the selected angle until the guide pin is removed.

35. The implant of claim 34 wherein:
the selected angle is an acute angle; and
the stop position of the facet stop lever is substantially perpendicular to the longitudinal axis of the first elongated shaft.

36. The implant of claim 35 including a dilator adapted to be delivered to a facet joint over the guide plate, wherein the dilator comprises:
a second elongated shaft having a longitudinal axis, a third end, and a fourth end; and
a guide plate track extending through the second elongated shaft between the third end and the fourth end, wherein the guide plate track is adapted to receive the first elongated shaft of the guide plate;
wherein the third end comprises a facet contact surface oriented at an oblique angle relative to the longitudinal axis of the second elongated shaft and adapted to engage exterior facets surfaces of vertebrae adjacent to a facet joint;
wherein the facet contact surface comprises a vertical slot adapted to engage the facet stop lever of the guide plate.

37. The implant of claim 35 including a drill guide adapted to be delivered over the guide plate and to facilitate drilling boreholes in the exterior facets surfaces of the vertebrae adjacent to a facet joint in which the implant is to be inserted for fastening the inter-facets plate, wherein the drill guide comprises:
a third elongated shaft having a longitudinal axis, a fifth end, and a sixth end;
a guide plate track extending through the third elongated shaft between the fifth end and the sixth end substantially along the longitudinal axis of the third elongated shaft, wherein the guide plate track is adapted to receive the first elongated shaft of the guide plate;
a first drill track and a second drill track positioned relative to the guide plate track in accordance with selected drilling positions in the exterior facets surfaces of the vertebrae adjacent to the facet joint;
wherein the fifth end comprises a facet contact surface oriented at an oblique angle relative to the longitudinal axis of the third elongated shaft and adapted to engage the exterior facets surfaces of the vertebrae adjacent to the facet joint;
wherein the facet contact surface comprises an inwardly directed facet joint curve adapted to be positioned approximately adjacent to the posterior entrance to the facet joint when the facet contact surface is in engagement with the exterior facets surfaces;
wherein the facet contact surface comprises a vertical groove adapted to engage the facet stop lever of the guide plate.

38. An implant for a cervical intervertebral facet joint, comprising:
first and second plates spaced apart in opposition and each having a first end and a second end;
a diverting member positioned between the first and second plates and moveable in engagement with the first and second plates in a direction between the first end and the second end of the first and second plates;
a driving member coupled with the diverting member, wherein the driving member is operable to cause the diverting member to move in the direction between the first end and the second end of the first and second plates to cause the plates to divert away from each other at and near their respective first ends without diverting away from each other at their respective second ends;
wherein the implant is adapted for insertion in a facet joint, wherein the implant has a first state in which the first ends of the respective first and second plates are not diverted away from each other and a second state in which the first ends of the respective first and second plates are diverted away from each other, wherein the implant is adapted in the first state to be inserted in a facet joint, and wherein the implant is operable in the second state to cause anterior distraction of a facet joint without inducing kyphosis; and
an inter-facet plate, wherein the inter-facet plate is:
engaged with the driving member;
adapted to be fastened to the external posterior facet surfaces of the vertebrae adjacent to a cervical intervertebral facet joint in which the implant is to be inserted; and
operable in response to operation of the driving member causing the plates of the implant to divert away from each other to substantially lock the external posterior facets of the adjacent vertebrae together to prevent posterior distraction of the facet joint;
adapted to be oriented with respect to the first and second plates to span the posterior opening of the facet joint in which the implant is to be inserted, and comprises an adjustment slot adapted to allow the position of the implant to be adjusted vertically and angularly relative to the inter-facet plate.

39. The implant of claim 38 wherein the inter-facet plate comprises:
  a surface adapted to face the external posterior facet surfaces of a first vertebra and a second vertebra adjacent to the facet joint in which the implant is to be inserted;
  a first pin having a base attached to the surface and adapted to be inserted into the external posterior facet surface of the first vertebra adjacent to the facet joint in which the implant is to be inserted; and
  a second pin having a base attached to the surface and adapted to be inserted into the external posterior facet surface of the second vertebra adjacent to the facet joint in which the implant is to be inserted.

40. An implant for a cervical intervertebral facet joint, comprising:
  first and second plates spaced apart in opposition and each having a first end and a second end;
  a diverting member positioned between the first and second plates and moveable in engagement with the first and second plates in a direction between the first end and the second end of the first and second plates;
  a driving member coupled with the diverting member, wherein the driving member is operable to cause the diverting member to move in the direction between the first end and the second end of the first and second plates to cause the plates to divert away from each other at and near their respective first ends without diverting away from each other at their respective second ends;
  wherein the implant is adapted for insertion in a facet joint, wherein the implant has a first state in which the first ends of the respective first and second plates are not diverted away from each other and a second state in which the first ends of the respective first and second plates are diverted away from each other, wherein the implant is adapted in the first state to be inserted in a facet joint, and wherein the implant is operable in the second state to cause anterior distraction of a facet joint without inducing kyphosis; and
  a guide plate for facilitating the delivery of devices adapted to prepare a facet joint to receive the implant, wherein the guide plate comprises:
    a first elongated shaft having a longitudinal axis, a first end and a second end, wherein the first end comprises a head adapted for posterior insertion in a facet joint;
    a guide pin passage extending through the first elongated shaft between the first end and the second end and through the head for guiding the guide plate;
    an elongated facet stop lever pivotably attached to the first elongated shaft near the first end, wherein the facet stop lever is adapted to pivot into a stop position and to engage exterior facets surfaces of the vertebrae adjacent to a facet joint in which the implant is to be inserted to prevent over-insertion of the shaft.

* * * * *